US012569624B2

(12) United States Patent
Lee-Sepsick et al.

(10) Patent No.: US 12,569,624 B2
(45) Date of Patent: Mar. 10, 2026

(54) DEVICES, METHODS AND COMPOSITIONS FOR REPRODUCTIVE ORGANS

(71) Applicant: Femasys Inc., Suwanee, GA (US)

(72) Inventors: Kathy Lee-Sepsick, Suwanee, GA (US); Jeremy Sipos, Alpharetta, GA (US)

(73) Assignee: Femasys Inc., Suwanee, GA (US)

( * ) Notice: Subject to any disclaimer, the term of this patent is extended or adjusted under 35 U.S.C. 154(b) by 0 days.

(21) Appl. No.: 18/292,749

(22) PCT Filed: Sep. 11, 2022

(86) PCT No.: PCT/US2022/043170

§ 371 (c)(1),
(2) Date: Jan. 26, 2024

(87) PCT Pub. No.: WO2023/039229

PCT Pub. Date: Mar. 16, 2023

(65) Prior Publication Data

US 2024/0358409 A1 Oct. 31, 2024

Related U.S. Application Data

(60) Provisional application No. 63/242,830, filed on Sep. 10, 2021.

(51) Int. Cl.
*A61M 5/315* (2006.01)
*A61B 17/43* (2006.01)
(Continued)

(52) U.S. Cl.
CPC ......... *A61M 5/31586* (2013.01); *A61B 17/43* (2013.01); *A61B 17/435* (2013.01);
(Continued)

(58) Field of Classification Search
CPC ........ A61M 5/31586; A61M 25/10182; A61M 5/31505; A61M 25/0026; A61M 25/0097;
(Continued)

(56) References Cited

U.S. PATENT DOCUMENTS

| | | | |
|---|---|---|---|
| 4,673,161 A | 6/1987 | Flynn et al. | |
| 5,372,584 A | 12/1994 | Zink | |

(Continued)

FOREIGN PATENT DOCUMENTS

| | | |
|---|---|---|
| AU | 2022343183 | 2/2024 |
| BR | 112024002943 | 6/2024 |

(Continued)

OTHER PUBLICATIONS

International Search Report, issued Jan. 11, 2023, in PCT/US2022/43170, Applicant Femasys Inc., 3 p., 24P1.

(Continued)

*Primary Examiner* — Phillip A Gray
(74) *Attorney, Agent, or Firm* — Mary Anthony Merchant; Schwegman Lundberg & Woessner, P.A.

(57) ABSTRACT

Disclosed herein are exemplary medical devices for delivery of compositions to a target site. A disclosed medical device may comprise a delivery device comprising a delivery device comprising a handle, a composition delivery container and its plunger, an insertion tube, a dual lumen catheter comprising an exit port and optionally, an end structure, and fluid connections therefor, components for moving one or more catheters or for compressing one or more catheters. Methods of treatment and diagnosis using a disclosed delivery device, compositions for such methods and kits and systems are also disclosed.

11 Claims, 9 Drawing Sheets

(51) Int. Cl.

| | |
|---|---|
| *A61B 17/435* | (2006.01) |
| *A61M 25/00* | (2006.01) |
| *A61M 25/06* | (2006.01) |
| *A61M 25/10* | (2013.01) |
| *A61M 31/00* | (2006.01) |
| *A61B 17/42* | (2006.01) |

(52) U.S. Cl.

CPC .... *A61M 5/31505* (2013.01); *A61M 25/0026* (2013.01); *A61M 25/0097* (2013.01); *A61M 25/0662* (2013.01); *A61M 25/10182* (2013.11); *A61M 31/00* (2013.01); *A61B 2017/4233* (2013.01); *A61M 2025/0008* (2013.01); *A61M 2025/0057* (2013.01); *A61M 2025/0681* (2013.01); *A61M 2025/1052* (2013.01); *A61M 2025/1061* (2013.01)

(58) Field of Classification Search

CPC ... A61M 25/0662; A61M 31/00; A61B 17/43; A61B 17/435

USPC .......................................................... 600/36

See application file for complete search history.

(56)                    References Cited

U.S. PATENT DOCUMENTS

| | | | |
|---|---|---|---|
| 5,624,399 A | 4/1997 | Ackerman | |
| 6,290,672 B1 | 9/2001 | Abae | |
| 9,238,127 B2 | 1/2016 | Lee-sepsick | |
| 12,268,855 B2 | 4/2025 | Lee-sepsick et al. | |
| 2004/0019323 A1* | 1/2004 | Carter ............. A61M 25/10187 | |
| | | | 604/97.03 |
| 2005/0045184 A1 | 3/2005 | Khera et al. | |
| 2012/0046260 A1* | 2/2012 | Lee-Sepsick ...... A61B 17/1219 | |
| | | | 514/249 |
| 2020/0121857 A1* | 4/2020 | Despa ............... A61M 5/31595 | |
| 2024/0335618 A1 | 10/2024 | Lee-sepsick et al. | |
| 2025/0161585 A1 | 5/2025 | Lee-sepsick et al. | |

FOREIGN PATENT DOCUMENTS

| | | |
|---|---|---|
| CA | 3228325 | 3/2023 |
| CN | 117897107 | 4/2024 |
| EP | 4398824 | 7/2024 |
| HK | 40109195 | 11/2024 |
| JP | 2024533079 | 9/2024 |
| KR | 20240053573 | 4/2024 |
| TH | 2401001348 | 5/2025 |
| WO | 0029060 | 5/2000 |
| WO | PCT/US22/043170 | 3/2023 |

OTHER PUBLICATIONS

Written Opinion, issued Jan. 11, 2023, in PCT/US2022/43170, Applicant Femasys Inc., 8 p., 24P1.

"European Application Serial No. 22868161.5, Extended European Search Report mailed Apr. 9, 2025", 8 pgs.

"International Application Serial No. PCT US2022 043170, International Preliminary Report on Patentability mailed Mar. 21, 2024", 10 pgs.

"European Application Serial No. 22868161.5, Response to Communication pursuant to Rule 1612 and 162 EPC filed Oct. 17, 2024", 8 pgs.

"Thailand Application Serial No. 2401001348, Office Action mailed Sep. 27, 2024", W English Translation, 8 pgs.

"Thailand Application Serial No. 2401001348, Response filed Dec. 26, 2024 to Office Action mailed Sep. 27, 2024", W English Claim, 16 pgs.

"U.S. Appl. No. 18/443,798, Non Final Office Action mailed Aug. 29, 2024", 9 pgs.

"U.S. Appl. No. 18/443,798, Response filed Nov. 14, 2024 to Non Final Office Action mailed Aug. 29, 2024", 13 pgs.

"U.S. Appl. No. 18/443,798, Notice of Allowance mailed Dec. 27, 2024", 8 pgs.

"U.S. Appl. No. 18/443,798, Corrected Notice of Allowability mailed Mar. 10, 2025", 6 pgs.

"Thai Application Serial No. 2401001348, Voluntary Amendment Filed May 29, 2025", W English Claims, 45 pgs.

"Japanese Application Serial No. 2024-513239, Voluntary Amendment filed Sep. 9, 2025", W English Claims, 13 pgs.

"Korean Application No. 10-2024-7003760, Voluntary Amendment filed Aug. 28, 2025", W English Claims, 14 pgs.

"European Application Serial No. 22868161.5, Response filed Oct. 21, 2025 to Extended European Search Report mailed Apr. 9, 2025", w claims, 5 pgs.

\* cited by examiner

DEVICES, METHODS AND COMPOSITIONS FOR REPRODUCTIVE ORGANS

CROSS-REFERENCE TO RELATED APPLICATIONS

The present disclosure is a U.S. National Stage Filing under 35 U.S.C. 371 from International Application No. PCT/US2022/043170, filed on Sep. 11, 2022, and published as WO 2023/039229, which is a PCT application claiming the priority to and benefit of U.S. Provisional Patent Application Ser. No. 63/242,830, filed Sep. 10, 2021, which is herein incorporated in its entirety. Any and all application for which a foreign or domestic priority claim is identified in the Application Data Sheet as filed with the present application are hereby incorporated by reference.

TECHNICAL FIELD

The present disclosure comprises devices, methods, compositions, systems and kits for providing compositions, such as biological or therapeutic compositions to mammalian structures, for example, to the uterine cornua and proximal ostium of one or more fallopian tubes.

BACKGROUND OF THE INVENTION

Infertility, often defined as not being able to get pregnant after trying for one year, can be a difficult situation for individuals and couples. It is estimated 15% of couples will have trouble conceiving. Globally, 48.5 million couples will experience infertility at some time, and in the United States, about nine percent of men and ten percent of women, aged 15 to 44, have reported infertility problems. Additionally, there appears to a rapid decline in male sperm counts, which has been referred to as the male fertility crisis. The earliest indications of this decrease first emerged in the 1970s. From this period, there has been a steady decline of about 1.4% in sperm counts with an overall decline of 52.4% over approximately 40 years. The most affected populations are found in countries or areas such as New Zealand, Australia, Europe and North America. A reduction in other parts of the world has yet to be observed. Such an increase in infertility in both sexes, in addition to decreased sperm counts or semen quality in males and blockage of at least one fallopian tube in females, has created a higher demand for methods of treating infertility and devices, systems and compositions that can aid in increasing fertility.

In medical and research application, there are many clinical situations where it is desired or necessary to deliver or transfer substances within a body tube or conduit by using a device. It is often desirable for treatment or diagnostic purposes. Unfortunately, many delivery techniques are challenging or not optimal to achieve the desired therapeutic treatment or diagnostic evaluation.

What is needed are devices, systems, methods, compositions, systems and kits that deliver therapeutic or active agents or that can be used for gynecological or infertility treatment and diagnosis.

BRIEF SUMMARY OF THE INVENTION

The present disclosure provides devices, systems, methods, compositions and kits for providing treatments and materials to a conduit, such as a mammalian fallopian tube. Such treatments and materials may be used to diagnose or treat infertility in mammals, and/or to establish a fertile state in a female, such as a female mammal; and/or provide therapeutic or active agents. An aspect of the present disclosure is to provide devices, systems, methods and compositions to a female mammal so that the female mammal becomes pregnant with one or more offspring.

The present disclosure provides a delivery device comprising a handle, a composition delivery container and its plunger, an insertion tube, a dual lumen catheter comprising an exit port and optionally, an end structure, and fluid connections therefor. A handle may be formed from a casing that defines a hollow interior for containing components of the device. A casing may comprise a first side and a second side that are joined at the edges to form a hollow handle wherein the first and second sides are similar, mirror images of each other. The dual lumen catheter has two lumens. One lumen is an distension lumen or distension catheter, which provides a medium such as air, gas or liquid, to the end structure of the dual lumen catheter, for example, to a balloon. A device may further comprise a distension syringe and plunger for providing distension medium to the end structure. The other lumen is a delivery lumen or delivery catheter having an exit port through which one or more compositions may be drawn into the device and also through which one or more compositions may be delivered from the device to a target site, for example, to a mammalian structure such as the cornua of an uterus or proximal ostium of a fallopian tube. A delivery device may comprise a component, e.g., a chamber, wherein a composition delivery catheter and a distension catheter are adjoined adjacently to form a dual lumen catheter. A delivery device may further comprise components for moving one or more catheters and/or for compressing one or more catheters.

The present disclosure provides methods for providing disclosed compositions to a target site. For example, a method for providing a disclosed composition may comprise providing a composition to a target site using a delivery device disclosed herein. In summary, a composition is loaded into a disclosed device by placing the exit port of the dual lumen catheter in the composition and moving the proximal end of the plunger of a delivery container in a proximal direction (e.g., moving the plunger in an outward direction from the device and toward the user) to create a suction force that moves at least a portion of the composition into the delivery catheter/lumen of the dual lumen catheter. A delivery device containing the composition may be provided to a subject, such as a mammalian female, by placing the tip of the insertion tube at the fundus of the subject's uterus and extending the distal end of the dual lumen catheter through the catheter exit port so that the end structure of the dual lumen catheter and the dual lumen catheter exit port are at or adjacent to the target site. The distension catheter/lumen is used to inflate the end structure, if so needed. The plunger of the delivery container is then moved in a distal direction through the delivery container (away from the user) so as to move at least a portion of the composition out of the dual lumen catheter exit port and to the target site. The device may or may not remain at the site for a predetermined time period. The device may be removed from the subject, and optionally before removal, the end structure is deflated, if needed, and the distal end of the dual lumen catheter is withdrawn to or into the insertion tube before withdrawing the insertion tube from the subject. Instead of removal, the device may be used to provide at least a portion of the remaining composition in the delivery catheter/lumen to another fallopian tube, by deflating the end structure, if needed, withdrawing the distal end of the dual lumen catheter to or into the insertion tube, rotating the device, extending the distal end of the dual lumen catheter so that the end structure of the dual lumen catheter and the dual lumen catheter exit port are at or adjacent to the second target site, inflating the end structure, if needed, and providing at least a portion of the composition to the second target site. In this method, both fallopian tubes can be treated. This method may be repeated one or more times, such as sequentially at the same treatment time (e.g., the same timeframe as the above method comprising one or two treatments, or over multiple treatment times that may be minutes, hours, days, weeks, months or years apart.

The present disclosure provides compositions that may be delivered by a disclosed delivery device. Compositions may comprise mammalian gametes, mammalian sperm, one or more mammalian ovum; and/or one or more mammalian fertilized ovum, zygotes or embryos, and/or combinations thereof, which may further comprise a pharmaceutical composition. Compositions may comprise treatment medications, active agents, biological agents, diagnostic agents, and other known agents and medications for treatment and diagnostic compositions, for example, for gynecological and obstetrical conditions, and/or combinations thereof, which may further comprise a pharmaceutical composition.

The present disclosure provides systems comprising a delivery device disclosed herein, comprising a handle, a composition delivery container and its plunger, an insertion tube, a dual lumen catheter comprising an exit port and optionally, an end structure, and fluid connections therefor. A disclosed device may or may not include a distension syringe for inflating an end structure, if distension is needed. Thus, a system may further comprise a syringe that can form a fluid mating with a disclosed device to provide a distension medium for inflating the end structure of the dual lumen catheter. A system may further comprise the delivery device comprising a component, e.g., a catheter chamber, wherein a composition delivery catheter and a distension catheter are adjoined adjacently to form a dual lumen catheter. A system may further comprise the delivery device comprising components for moving one or more catheters and/or for compressing one or more catheters. A system may further comprise one or more compositions to be delivered by the delivery device. In an aspect, a system may comprise a handle, a composition delivery container and its plunger, an insertion tube, a dual lumen catheter comprising an exit port and optionally, an end structure, a composition, and fluid connections therefor. The system may further comprise the delivery device comprising a component, e.g., a chamber, wherein a composition delivery catheter and a distension catheter are adjoined adjacently to form a dual lumen catheter. A system may further comprise the delivery device comprising components for moving one or more catheters and/or for compressing one or more catheters.

The present disclosure provides a kit comprising a disclosed delivery device comprising a handle, a composition delivery container and its plunger, an insertion tube, a dual lumen catheter comprising an exit port and optionally, an end structure, and fluid connections therefor. A delivery device may comprise a component, e.g., a chamber, wherein a composition delivery catheter and a distension catheter are adjoined adjacently to form a dual lumen catheter. A delivery device may further comprise components for moving one or more catheters and/or for compressing one or more catheters. A kit may further comprise instructions for use and/or assembly of a disclosed device. A kit may further comprise a distension syringe for inflating an end structure, if distension is desired. Thus, a kit may further comprise a syringe that can form a fluid mating with a disclosed device to provide an element for inflating the end structure of the dual lumen catheter. A kit may comprise one or more compositions for diagnosis or treatment of a gynecological or obstetrical condition of a mammal. A kit may comprise one or more compositions that are useful for the operation of a delivery device, for example, sterile saline. A kit may provide a disclosed delivery device and/or the kit components above in combined sterile packaging or individually in separate sterile packagings.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments and aspects are set forth in the description below. The features illustrated or described in connection with one exemplary embodiment or aspect may be combined with the features of other embodiments or aspects. Thus, any of the various embodiments or aspects described herein can be combined to provide further embodiments of the present disclosure. Features of the embodiments and aspects can be modified, if necessary, to employ concepts of the various patents, applications and publications as identified herein to provide yet further embodiments. Other features, objects and advantages will be apparent from the description, the drawings, and the claims.

BRIEF DESCRIPTION OF THE DRAWING(S)

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

Figures 6A, 6B:
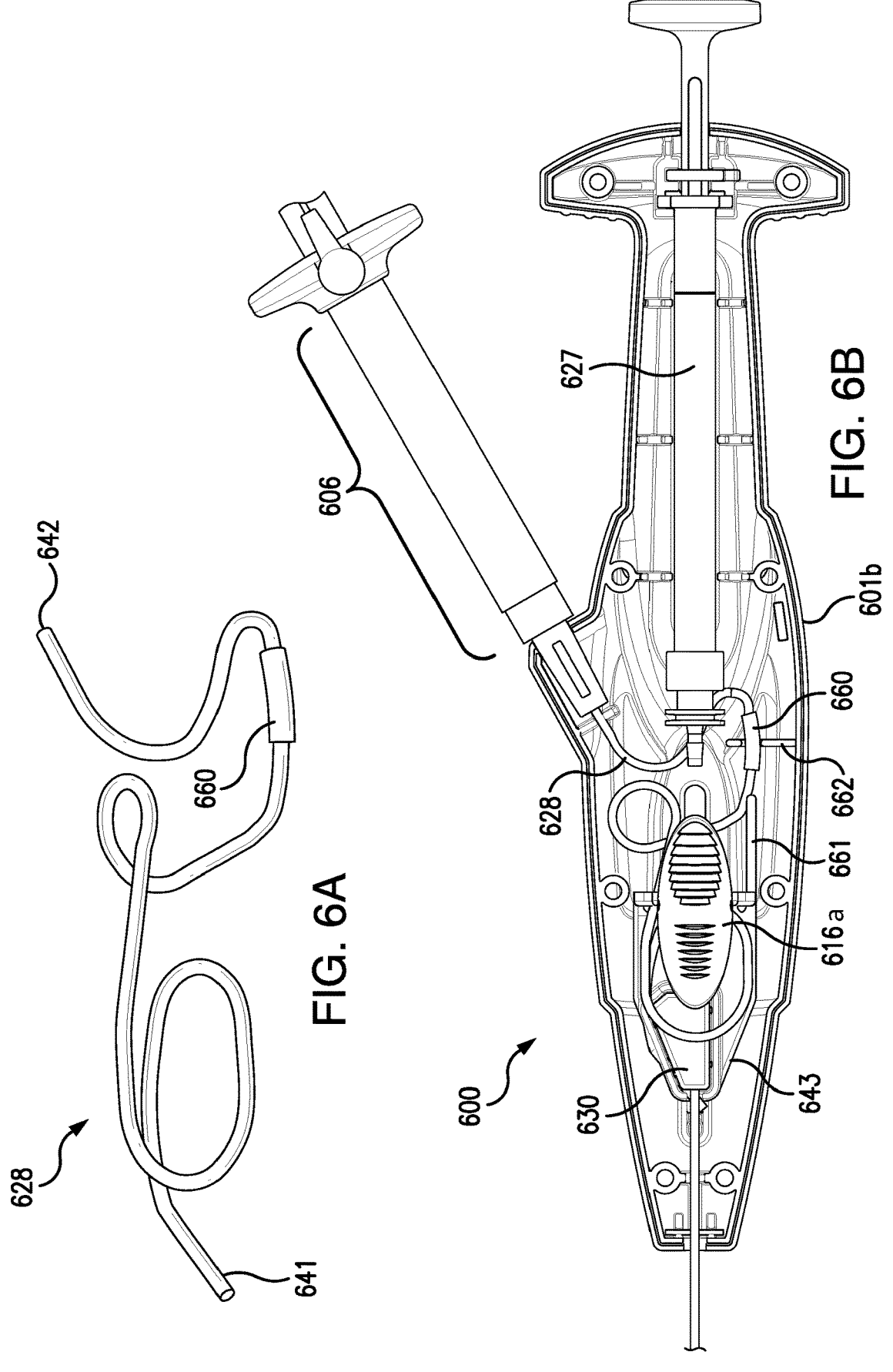
Figures 6C, 6D:
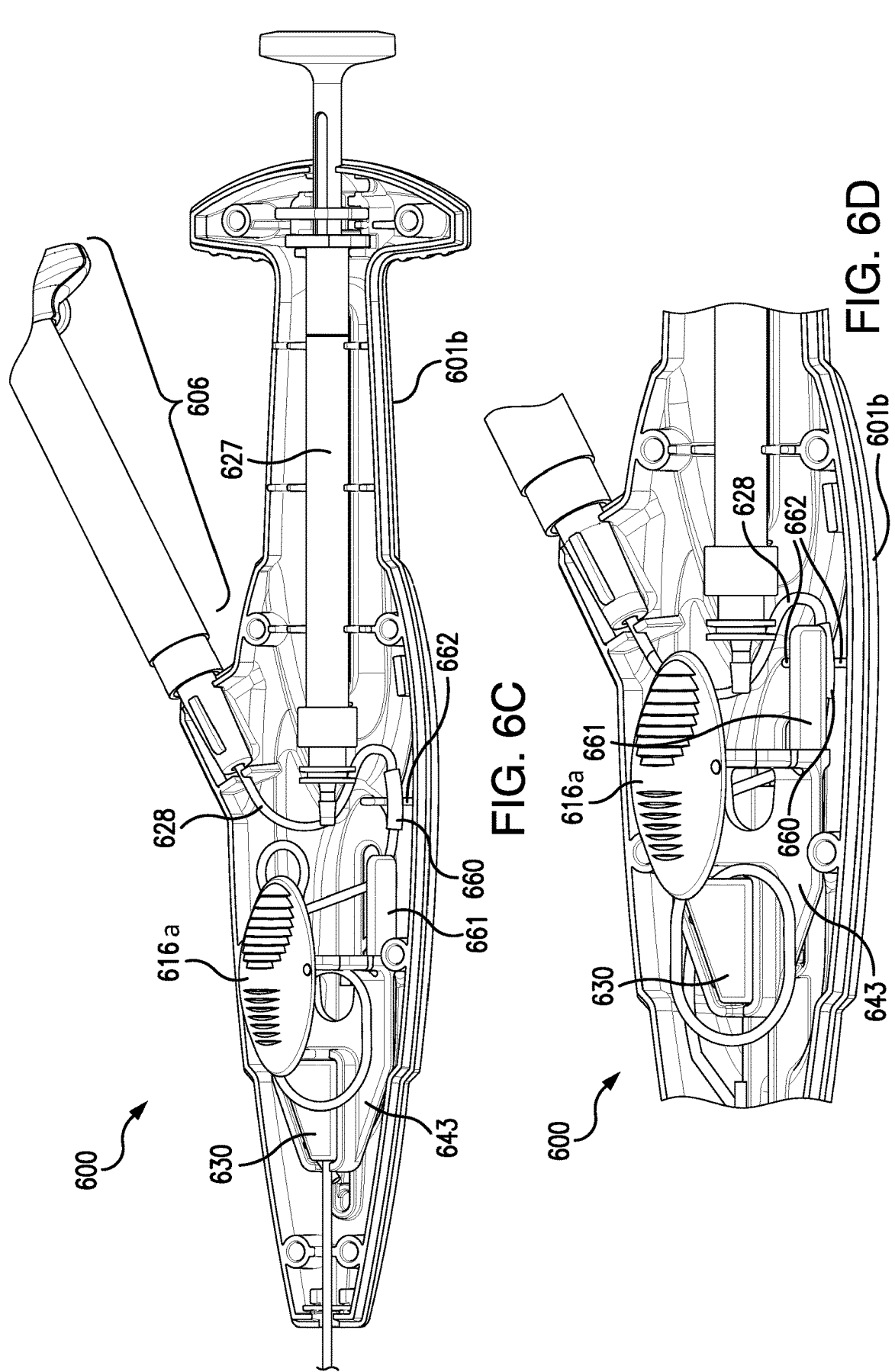

FIG. 6A shows an isolated view of a portion of an alternative distension catheter having an enlarged section located distally to, and removed from, the proximal end, and FIG. 6B shows the placement of this portion of the alternative distension catheter within the casing of an exemplary delivery device. FIG. 6C shows a closer view of the interior of a casing of an exemplary delivery device wherein the catheter carrier rod is not engaged with the alternative distension catheter. FIG. 6D shows an enlarged view of the interior of a casing of an exemplary delivery device with the catheter carrier rod engaged to compress the alternative distension catheter.

Figure 7A:
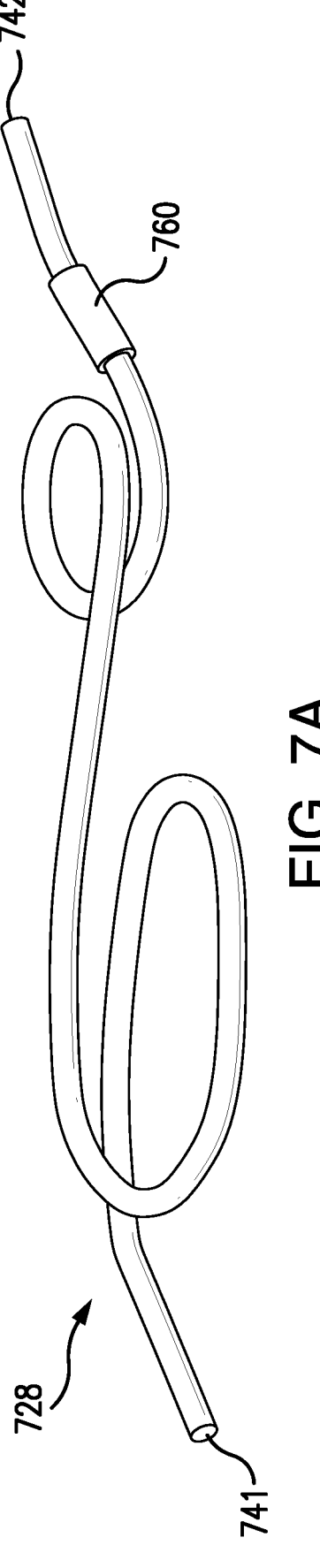
Figure 7B:
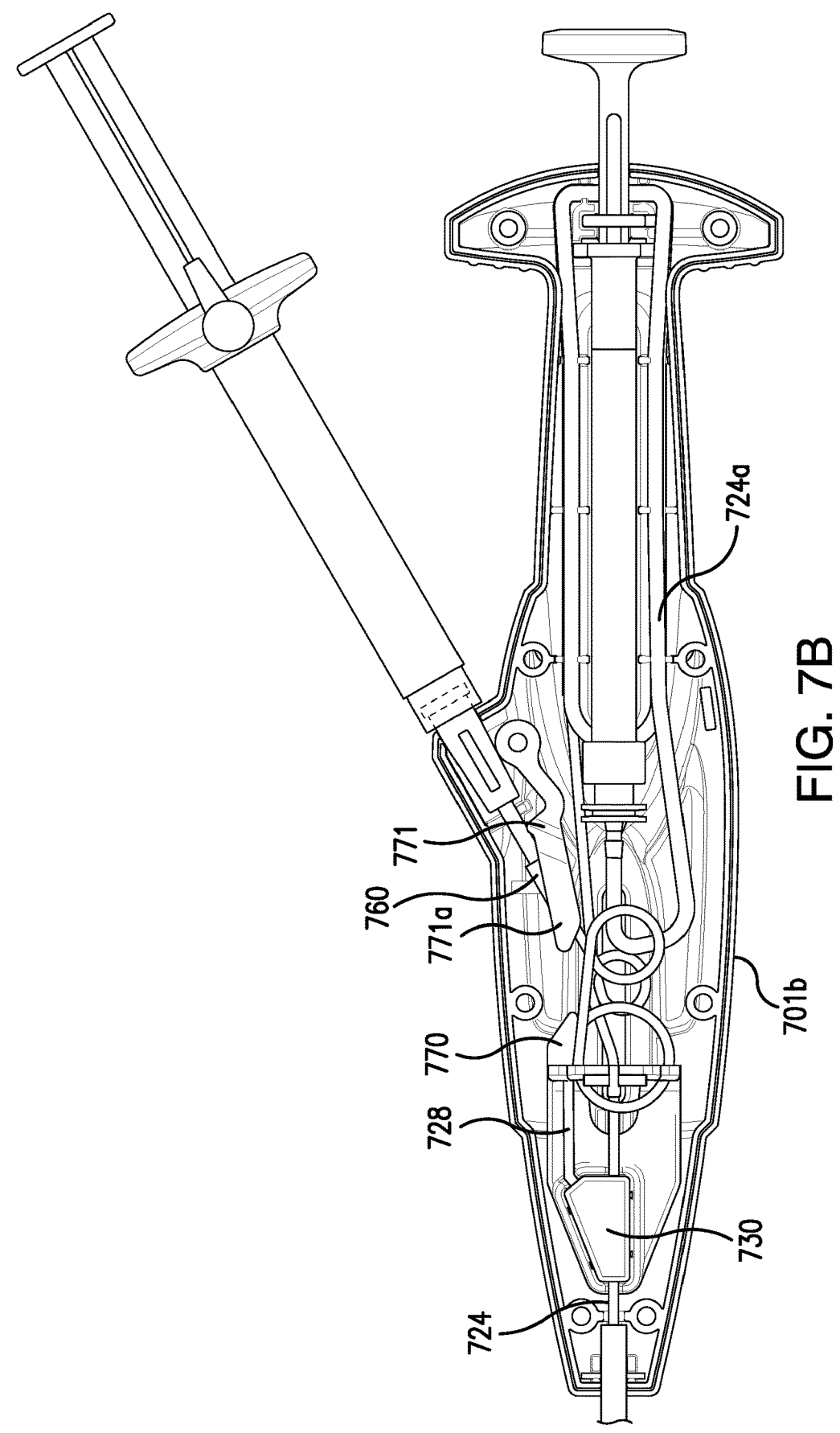

FIG. 7A shows an isolated view of a portion of a second alternative distension catheter having an enlarged section located closely to and almost adjacent to the proximal end. FIG. 7B shows the interior of a casing of an exemplary delivery device and illustrates a compression lever engaged with the enlarged section of the second alternative distension catheter for control of the distension catheter.

DETAILED DESCRIPTION

The present disclosure provides devices, systems, methods, kits and compositions for providing treatments and/or materials to a conduit, such as a mammalian fallopian tube. In an aspect, a delivery device comprises a handle, a composition delivery container, an insertion tube, a dual lumen catheter, and fluid connections therefor. A disclosed device may further comprise a distension syringe. A handle may be formed from a casing that defines a hollow interior for containing components of the device. A casing may comprise a first side and a second side that are joined at the edges to form a hollow handle wherein the first and second sides are similar images of each other. See FIG. 1 for an exemplary view of one side of a casing forming a handle.

A delivery device may further comprise a component, e.g., a catheter chamber, wherein a composition delivery catheter and a distension catheter are adjoined adjacently to form a dual lumen catheter. A delivery device may further comprise components for moving one or more catheters and/or for compressing one or more catheters.

In an aspect, the present disclosure provides a delivery device comprising a handle, a composition delivery container, for example, comprising a composition delivery container syringe and its plunger, an insertion tube, a dual lumen catheter comprising an end structure, components for moving the dual lumen catheter outwardly from and inwardly toward the insertion tube, optionally, components for distending the end structure, and fluid connections therefor. A handle may be formed from a casing that defines a hollow interior for containing components of the device. A casing may comprise a first side and a second side that are joined at the edges to form a hollow handle wherein the first and second sides are similar images of each other. The features and/or components that are found on the exterior side of one side of the casing are replicated or also found on the exterior side of the other side of the casing. Most, if not all, components found on the interior of the casing are singular and are not duplicated or replicated within the casings. The figures herein can be used to show these components. The dual lumen catheter has two lumens. One lumen is a distension lumen or distension catheter, which provides a medium such as air, gas or liquid, to the end structure of the dual lumen catheter, for example, to a balloon. The other lumen is a composition delivery lumen or composition delivery catheter having an exit port, which is herein referred to as the exit port of the dual lumen catheter, through which one or more compositions may be drawn into the delivery device and also through which one or more compositions may be delivered from the delivery device to a target site, for example, to a mammalian structure such as the cornua of an uterus or proximal ostium of a fallopian tube. A delivery device may further comprise components for moving one or more catheters or for compressing one or more catheters.

In an aspect, a delivery device further comprises components so that the delivery device can intake all or a portion of a composition into the delivery device through the exit port of a dual lumen catheter (for example by suction force, from the delivery container, into the exit port of the dual lumen catheter), and then, once the exit port is located at the target site, return all or a portion of the composition taken into the delivery device out of the delivery device through the same exit port of the dual lumen catheter. A delivery device may also comprise components for placement of the exit port, components for movements of catheters, components for control of catheters' movements, and if needed, components for distension of the end structure of the dual lumen catheter and components for control of the distension of an end structure.

In an aspect, a delivery device comprises a handle formed by a casing to form a hollow handle. For example, a handle may be formed by adjoining two casing sides, which sides have features or structures that are replicated on each side. A handle encloses the composition delivery container, which comprises a container and a slidably disposed component therein, such as a plunger, for moving a composition into and through the exit port of a dual lumen catheter having a composition delivery catheter in fluid connection with the composition delivery container, and also out of the exit port of the dual lumen catheter having a composition delivery catheter in fluid connection with the composition delivery container. Both movements, into and out of the delivery device, of the composition are through the exit port of the dual lumen catheter having a composition delivery catheter in fluid connection with the composition delivery container. The handle also provides a distension inlet port for attachment of a distension syringe, comprising a plunger, which is in fluid connection with the end structure of the dual lumen catheter.

The composition delivery catheter forms one lumen of the dual lumen catheter of the delivery device. A dual lumen catheter is used for providing both a distension medium to the dual lumen catheter end structure, such as a balloon, by using one lumen, and for providing a composition to a target site, using the other lumen. Herein, the two lumens of a dual lumen catheter may be referred to as "catheters", wherein one lumen of the dual lumen catheter is used for transport of a distention medium, herein referred to as an "distension catheter", and the other lumen of the catheter of the dual lumen catheter is referred to as a "composition delivery catheter" and is intended for transport of a composition, such as a treatment or diagnostic composition. The distension catheter and the delivery catheter are adjacently attached to one another in the catheter chamber of the delivery device to form the dual lumen catheter. It is to be understood that the exit port of the dual lumen catheter is the distal end of the delivery catheter and is referred to herein as the exit port of the dual lumen catheter.

Though the distension inlet port, distension syringe and/or plunger, may be referred to as "an air inlet port" or "air syringe and/or plunger" it is intended that these distension structures can also function to provide a liquid composition, such as saline, as a distension medium. Thus, the distension inlet port is a port for air, gas or liquid compositions such as saline or water, that are in fluid connection, so that an air, gas or liquid composition, such as saline or water, provided in a liquid syringe, is used to inflate an end structure of the dual lumen catheter. Those of skill in the art know that where "air" is used, a liquid composition, such as saline or water, may be also intended.

A composition delivery container may be a container comprising a syringe body with a syringe plunger slidably disposed therein (i.e., component for moving a composition into and out of the exit port of the dual lumen catheter). Movement in a proximal direction of the syringe plunger moves a composition into the exit port of the dual lumen catheter and into the composition delivery catheter's lumen so that the majority, if not all, of the composition remains in the composition delivery catheter and not in the composition delivery container. Once the composition is within the composition delivery catheter, movement in a distal direction of the syringe plunger moves the composition from the composition delivery catheter, through a portion of the lumen of the composition delivery catheter and out the dual lumen catheter exit port, for example, to a target site, for example, into the cornua of a mammalian uterus at the proximal ostium of a fallopian tube. Movement of the plunger can be seen in the window (an opening in each side casing for viewing the composition delivery container and location of the composition delivery plunger within the container) located in the midline axis of the casing of the handle, proximate in a distal direction from the finger grip. Optionally, an adjustable sliding marker may be placed on the window or be visible in the window to mark the amount of composition taken in or dispensed. The sliding marker provides a visual indicium of the amount of composition dispensed and may be used in combination with indicia, usually numerical markings, located on the edges of the window. Optional, and removable from device 100, is a distension syringe (air, gas or liquid syringe), which comprises a syringe body with a syringe plunger slidably disposed therein that moves air, gas or a liquid into and out of a distension catheter that is in fluid connection with the end structure of the dual lumen catheter, for example, to inflate and deflate an end structure, such as a balloon.

Located in the central axis (midline) of each of the first and the second side of a casing of the handle, and distal to the window, is a finger slide, slidably disposed within a slot (opening), found in each of the side casings. Each of the first side and the second side of the casing comprise a slot with a finger slide slidably disposed therein. The finger slide has an exterior surface and an interior surface, wherein the interior surface faces the outer surface of the handle casing. The interior surface of the finger slide is connected, via a prong, to the catheter carrier located within the interior of the handle. When the finger slide is moved in a proximal or distal direction, the catheter carrier is moved and the dual lumen catheter is moved. When the finger slide is moved in a distal direction, the exit port of the dual lumen catheter is moved away from or out of the catheter exit port of the insertion tube and extended from the insertion tube. When the finger slide is moved in a proximal direction, the exit port of the dual lumen catheter is moved toward the insertion tube and near or into the catheter exit port of the insertion tube.

Methods for delivery of one or more compositions to a conduit, such as to the uterine cornua and at the proximal ostium of a mammalian fallopian tube, are disclosed herein. In an aspect, a method may comprise a method for enhancing fertility in a subject by providing one or more compositions, for example, a male sperm composition to a target site, which may be adjacent to, and optionally at least partially into at least a portion of a female fallopian tube, for example, a target site such as the uterine cornua and at the proximal ostium of a fallopian tube, so that the sperm composition may more easily contact a female egg. In an aspect, a method for treatment of a subject may comprise providing one or more compositions comprising an effective amount of one or more therapeutic agents or active agents to the uterine cornua and at the proximal ostium of a fallopian tube, for example, by delivering the therapeutic or active agent composition to the uterine cornua and at the proximal ostium of the fallopian tube wherein at least a portion of the composition may contact at least a portion of the fallopian tube, thus providing treatment to at least at portion of the fallopian tube. In an aspect, a method for diagnosis of a condition in a subject may comprise providing one or more compositions comprising an effective amount of one or more radiographic or sonographic agents to the uterine cornua and at the proximal ostium of a fallopian tube, for example, by delivering one or more radiographic or sonographic compositions to the uterine cornua and at the proximal ostium of the fallopian tube wherein at least a portion of the composition may enter at least a portion of the fallopian tube, thus providing diagnostic visualization of at least a portion of the fallopian tube. Such compositions may comprise pharmaceutical compositions.

Systems disclosed herein may comprise disclosed delivery devices and components for accomplishing, for example, methods disclosed herein. The present disclosure provides systems comprising a delivery device disclosed herein, comprising a handle, a composition delivery container and its plunger, an insertion tube, a dual lumen catheter comprising an exit port and optionally, an end structure, and fluid connections therefor. A disclosed device may or may not include a distension syringe for inflating an end structure, if distension is needed. Thus, a system may further comprise a syringe that can form a fluid mating with a disclosed device to provide a distension medium for inflating the end structure of the dual lumen catheter. A system may further comprise the delivery device comprising a component, e.g., a catheter chamber, wherein a composition delivery catheter and a distension catheter are adjoined adjacently to form a dual lumen catheter. A system may further comprise the delivery device comprising components for moving one or more catheters or for compressing one or more catheters. A system may further comprise one or more compositions to be delivered by the delivery device. In an aspect, a system may comprise a handle, a composition delivery container and its plunger, an insertion tube, a dual lumen catheter comprising an exit port and optionally, an end structure, a composition, and fluid connections therefor. The system may further comprise the delivery device comprising a component, e.g., a chamber, wherein a composition delivery catheter and a distension catheter are adjoined adjacently to form a dual lumen catheter. A system may further comprise the delivery device comprising components for moving one or more catheters or for compressing one or more catheters.

Compositions are disclosed herein that may be delivered by delivery devices disclosed herein, and in methods disclosed herein. In an aspect, a composition may comprise at least one male sperm. In an aspect, a composition may comprise at least one therapeutic agent. In an aspect, a composition may comprise at least one active agent. Compositions may comprise further comprise pharmaceutical compositions and formulations.

The present disclosure provides kits comprising one or more disclosed delivery devices. The present disclosure provides a kit comprising a disclosed delivery device comprising a handle, a composition delivery container and its plunger, an insertion tube, a dual lumen catheter comprising an exit port and optionally, an end structure, and fluid connections therefor. A delivery device may comprise a component, e.g., a chamber, wherein a composition delivery catheter and a distension catheter are adjoined adjacently to form a dual lumen catheter. A delivery device may further comprise components for moving one or more catheters and/or for compressing one or more catheters. A kit may further comprise instructions for use and/or assembly of a disclosed device. A kit may further comprise a distension syringe for inflating an end structure, if distension is desired. Thus, a kit may further comprise a syringe that can form a fluid mating with a disclosed device to provide an element for inflating the end structure of the dual lumen catheter. A kit may comprise one or more compositions for diagnosis or treatment of a gynecological or obstetrical condition of a mammal. A kit may comprise one or more compositions that are useful for the operation of a delivery device, for example, sterile saline. A kit may provide a disclosed delivery device and/or the kit components above in combined sterile packaging or individually in separate sterile packagings.

Exemplary devices, methods, systems, compositions and kits can be understood by elements and components shown in the drawings. As used in the various figures herein, like numbers are used to describe like elements. As used herein proximal is closer to the user of the device and towards composition delivery container plunger end 103 of an exemplary device (see FIG. 1), and distal is the direction away from the user and towards, or beyond, tip 122 at the end of the insertion tube of an exemplary device (see FIG. 1).

Figure 1:
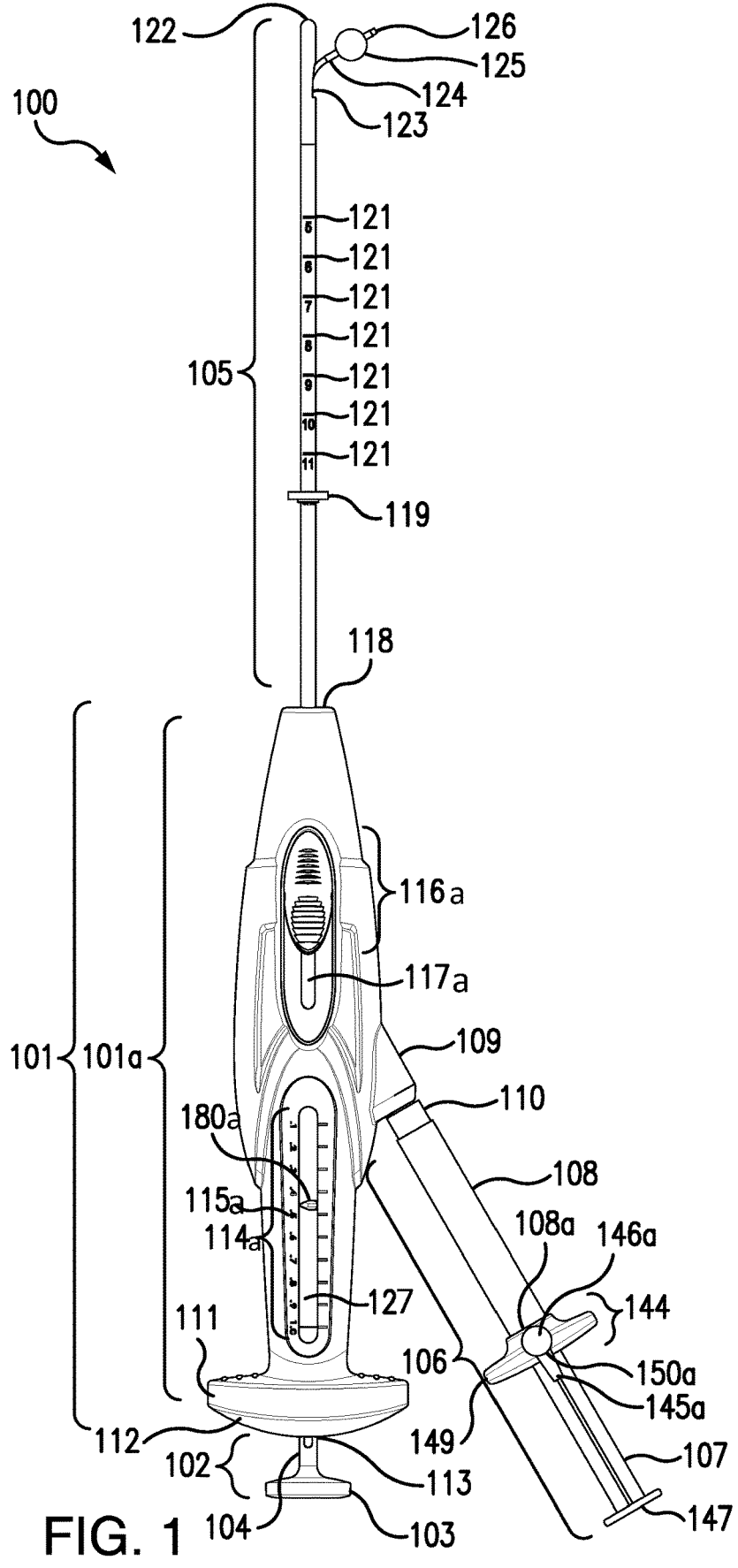
FIG. 1 shows an exemplary delivery device of the present disclosure, as seen from the first side of the device, which is the same as the image of the second and opposite side of the device, which is not shown.

FIG. 1 shows an exemplary device 100 of the present disclosure. Handle 101, composition delivery container plunger 102 and insertion tube 105 are shown. Handle 101 encloses composition delivery container 127, comprising a container, which may be a syringe body, in which composition delivery container plunger 102 is slidably disposed and which movingly seals the proximal opening of the composition container syringe body of composition delivery container 127. Proximal to handle 101 are seen composition delivery container plunger proximal end 103 and a portion of composition delivery container plunger stem 104. The remainder of composition delivery container plunger is slidably disposed within composition delivery container 127, which is within handle 101, and partially visible through window 114. Optionally, composition delivery container 127 is at least sufficiently transparent so that composition delivery container plunger stem 104 is visible through window 114. Optionally, indicia 115, such as numbers, are located on one or both vertical sides, parallel to the midline, of the window 114. Optionally, sliding marker 180 is visible at window 114 to aid in indicating an amount of the composition, once the composition is contained within the composition delivery catheter of the device, or to indicate the distance that the end of plunger 102 has moved.

Optional distension syringe 106 is shown with distension syringe plunger 107 extended proximally from distension syringe body 108, wherein distension syringe body 108 on its distal end is attached to syringe attachment 110, for example by a luer lock mating pair, to the proximal end of distension inlet port 109. Distension syringe plunger 107 movingly seals the open proximal end 108a of distension syringe body 108. The distal connector end (not shown) of distension syringe body 108 fluidly connects with distension catheter 228, shown in FIG. 2, in the interior of distension inlet port 109. Distension inlet port 109 is formed by a protrusion of side casing 101a (and a matching protrusion of side casing 101b (not shown). As shown, syringe attachment 110 comprises a luer lock as the connector for connecting distension syringe body 108 with distension inlet port 109 to form a fluid connection between syringe body 108 and distension catheter 228. Distension syringe 106 may be prefilled with air or gas or a liquid, such as saline or water. For example, distension inlet port 109 may comprise a female luer lock and distension syringe body 108 may comprise a male luer lock to form a fluid connection between distension syringe body 108 and distension catheter 228.

Optionally, distension syringe 106 may comprise syringe lock 144, which locks distension syringe plunger 107 in its distal most direction within distension syringe body 108, thus maintaining end structure 125 in a fully extended condition, e.g., a balloon inflated with air, gas or a liquid. Syringe lock 144 may comprise an end piece 149 that that is attached to and encircles the exterior of open proximal end 108a of distension syringe body 108. Movably affixed to end piece 149 are two finger pinch clamps 146a and 146b (not shown) that are spaced 180 degrees apart on the exterior edge of end piece 149. Only one finger pinch clamp is shown in FIG. 1. Each finger pinch clamp, 146a or 146b (not shown), is generally rectangular in shape, with two shorter sides and two longer sides, and with an outer surface facing away from end piece 149 and an inner surface facing toward end piece 149. A finger pinch clamp, e.g., 146a, is moveably attached to end piece 149 at a central location on the finger pinch clamp inner surface. One shorter end of pinch clamp 146a comprises a finger depression zone 150a and the opposite shorter end comprises a movable pincer 145a. Pinch clamp 146b similarly comprises a finger depression zone 150b and a moveable pincer 145b (not shown). Simultaneously applying pressure to both finger pinch clamps' (146a and 146b) finger depression zones 150a and 150b, displaces outwardly each moveable pincer 145a and 145b. When the moveable pincers 145a and 145b are moved outwardly, distension plunger head 147 can be moved distally so that distension plunger 107 is slidably positioned entirely within distension syringe body 108, and distension plunger head 147 is between pincer arms 145a and 145b. Releasing the pressure on finger depression zones 150a and 150b causes moveable pincer 145a and 145b to move inwardly, returning to their first position, and securing distension plunger head 147 within the two pincers, and thus preventing distension plunger 107 from further movement. An exemplary syringe lock 144 is shown in U.S. Design patent application Ser. No. 29/709,130, which is herein incorporated in its entirety.

Syringe lock 144 may be modified. For example, and not shown, alternative 150a and 150b depression zones each may be an extended into a rectangularly shaped flat lever arm and positioned so that each of alternative 150a and 150b lever arms are aligned with and extend away from pincer arms 145a and 145b. When depressed or moved towards syringe body 108, alternative 150a and 150b lever arms provide a larger surface and lever action for moving pincer arms 145a and 145b outwardly and away from plunger 107. In this position, plunger end 107 can be moved to its distal most position, between the opened pincer arms 145a and 145b. When the alternative 150a and 150b lever arms are released, plunger end 107 is "trapped" and held stationary by pincer arms 145a and 145b, thus providing a "lock" for the syringe 108 so that no distension medium can move within the delivery device or system.

Use of such a syringe lock 144 with distension syringe 108 and plunger 107 allows for control of the inflation of a catheter end structure without the use of a stopcock. For example, during use without a syringe lock or a stopcock or other interference in the distension tubing to stop distension medium moving in the distension catheter, an inflated end structure on a catheter lumen connected to the distension syringe, such as a balloon, exerts pressure backwards towards the distension syringe, which may push the distension syringe plunger in a proximal direction, thus decreasing the inflated size of the end structure. This reduction in the end structure's size, due to loss of air or fluid in the end structure, may allow the composition being delivered to flow away from the delivery target site. For example, the end structure of a dual lumen catheter of a disclosed device is designed to create a temporary barricade at the uterine cornua so that an isolated enclosure formed by the uterine cornua walls, the proximal ostium of the fallopian tube and the end structure. The delivered composition is deposited in this space, at the uterine cornua and at the proximal ostium of the fallopian tube, and potentially, at least a portion of the deposited composition flows into the fallopian tube and/or remains in that cornua of the uterus. For as long as the end structure is in place, at least the majority of the delivered composition does not flow away from that enclosed space, for example, does not flow into the larger space of the interior of the uterus. If the end structure is reduced in size or its shape is changed by reverse flow (in a proximal direction) of air or fluid from the end structure, the unique and/or valuable delivered composition could flow away from the uterine cornua and fallopian tube, and the intended treatment may fail. Use of a disclosed syringe lock can prevent the distension syringe plunger from being pushed proximally from the distension syringe body and prevent the reduction of the size or shape of the end structure. Use of a syringe lock may aid in ensuring that the treatment or diagnosis comprising the composition(s) to be delivered is properly administered by accurate and substantially complete delivery of the intended composition. Alternatively, an operator can maintain pressure on the distension syringe plunger 107 to maintain the shape of the end structure 125. Alternatively, a stopcock can be provided between distension inlet port 109 and syringe attachment 110.

Though not wishing to be bound by any particular belief, it is thought that the presence of an end structure of a delivery catheter provides a partially enclosed area so that once the end structure is in place in the uterine cornua and forming a structure that prevents passage to the rest of the uterus, that partially enclosed area is open at and to the proximal ostium of the fallopian tube, and the formation of the partially enclosed area by the end structure prevents flow of a delivered composition into the rest of the uterine cavity. Additionally, it is thought that providing the delivered composition to the partially closed area with only one outlet (the proximal ostium of the fallopian tube) results in a fluid pressure that helps drive the delivered composition through the proximal tubal ostium and at least into a portion of the fallopian tube.

Handle 101 is comprises a casing and may be assembled from two joined sides of a casing to form handle 101 and to define openings therein. As shown in FIG. 1, in an exemplary device, handle 101 comprises first side casing 101a and second side casing 101b (not shown in FIG. 1). First side casing 101a, and second side casing 101b, are generally concave in shape and fit together at each side's edge to form a hollow container, handle 101. Elements shown in FIG. 1 of handle 101, located on or in the exterior of first side casing 101a are replicated and similarly located on or in the exterior of, or interact with, the second side casing 101b, and for ease of understanding, elements on second side casing 101b not shown in FIG. 1, and though present in an exemplary device, these components will not be referred to in pairs of a and b throughout the following description. Elements that repeat on both the first side and the second side, 101a and 101b, include window 114, indicia 115, sliding marker 180, finger slide 116, and slot 117, and within handle 101, is slider prong 244 connecting each finger slide to the catheter slide. As the elements repeat, and only one side is shown, in general, when there are two identical elements, the shown side is "a" and the unshown side is "b". In other cases, one portion of an element may be referred to as "a", such as composition delivery catheter as 224a, and dual lumen catheter 224, which comprises a lumen that is composition delivery catheter 224a.

Handle 101 is shaped to form certain elements. Finger grip 111 is located at the proximal end 112 of handle 101 and can be formed by the mating of first casing 101a and second casing 101b. Proximal handle opening 113 is an opening that can be formed by the mating of first casing 101a and second casing 101b which mating adjoins two semi-circular cutouts, one in first casing 101a and one in second casing 101b, to create a circular opening, proximal handle opening 113, when mated. A similar arrangement of cutouts and mating of casing sides is found at the distal end of handle 101 to form distal handle opening 118 through which traverses insertion tube 105. Insertion tube 105 is a hollow tube having its open proximal end (205a in FIG. 2) inserted through distal handle opening 118 and which is attached in the interior of handle 105, and having a closed distal end forming tip 122. Adjacent to and removed in a proximal direction from tip 122, insertion tube 105 defines a catheter exit port 123, which is located off-center of an axis line drawn centrally through insertion tube 105 and handle 101. Optionally, a catheter sleeve (not shown), which is a hollow tube, may be disposed within and through all or a portion of the interior of insertion tube 105. Dual lumen composition delivery catheter 124 may reside within the catheter sleeve when catheter sleeve is present or dual lumen composition delivery catheter 124 may reside within insertion tube 105 if no catheter sleeve is present.

Proximal handle opening 113 allows composition delivery container plunger 102 to slidably move into and out of composition delivery container body 127 (located in the interior of handle 101) in a proximal and distal direction, to effectuate composition intake into and out of exit port 126 of dual lumen catheter 124. (shown in FIG. 2) Composition delivery container 127 (shown as a syringe body in FIG. 2), may be partially seen through window 114a, which is located along the central axis of handle 101 between finger grip 111 and slot 117a. One or more indicia 115a may be located on the lateral sides of window 114a. Optionally, window 114a may include sliding marker 180a that is movable in a proximal or distal direction, along the exterior of window 114a, and that is moved to the position that the distal end of composition delivery container plunger 102 is moved to when bringing a composition through exit port 126 and into composition delivery catheter 224a lumen of dual lumen catheter 124. This sliding indicator component can be used to show the amount of composition contained in the composition delivery catheter 224a or location of the distal end of composition container plunger 102. Finger slide 116a is located on the central axis of handle 101 and distally of window 114a, and is moveable, in a proximal to distal direction and in reverse, in a distal to proximal direction, within slot 117a.

Distal handle opening 118 is formed by the mating of casings 101a and 101b and allows for the traverse of insertion tube 105 from the interior of handle 101 outwardly and distally, along the central axis of handle 101. Insertion tube 105 may comprise depth stop 119 and one or more insertion tube indicia 121 (which may include more or fewer indicia than are shown in FIG. 1). Tip 122, which may be an atraumatic tip, is located at the distal end of insertion tube 105. Catheter exit port 123 is located proximate to tip 122, and is removed in a proximal direction from tip 122 and is offset from the central axis of insertion tube 105. Dual lumen catheter 124, comprises two lumens, one, the lumen of composition delivery catheter 224a for composition intake or outflow, and the second lumen as distension (air, gas or other fluid) catheter 228 for filling end structure 125, and is shown exiting catheter exit port 123. Dual lumen catheter 124 comprises end structure 125, and exit port 126, which is the distal end of composition delivery catheter 224a.

Figure 2:
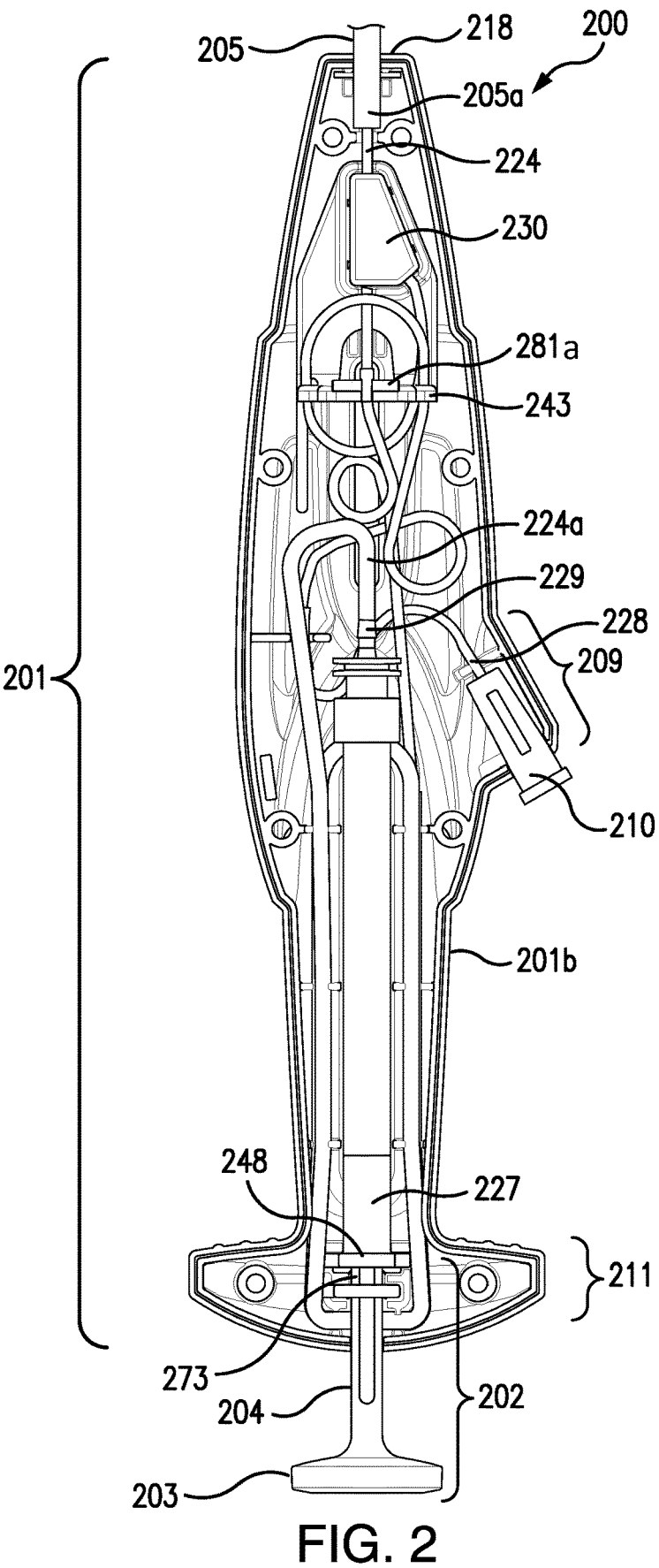
FIG. 2 shows the interior of an exemplary delivery device of the present disclosure, as seen with the first side casing removed to show the components' and catheters' arrangements within the device.

FIG. 2 shows the interior components of an exemplary device 200 of the present disclosure. Handle 201 is shown with first side of the casing removed, with the interior components residing within the interior of casing side 201b, which along with first casing 101a (shown in FIG. 1), forms a complete handle 201. Proximal end 205a of insertion tube 205 is shown in FIG. 2 and extends distally from handle 201 through distal handle opening 218. Distension inlet 209 is formed by a protrusion of handle 201b (and a matching protrusion of handle 201a (not shown) and contains the proximal end of distension catheter 228, which is shown in more detail in FIGS. 4A and 4B, and syringe attachment 210.

Components within the interior of handle 201 include composition delivery container 227, which is shown as a syringe body, within which composition delivery container plunger 202 is slidably disposed through syringe proximal end 248. Composition delivery container plunger 202 can be moved in a proximal direction, to draw a composition into composition delivery catheter 224a lumen of dual lumen catheter 224's exit port 126 (shown in FIG. 1) and also can be moved in a distal direction to push the composition out of composition delivery catheter 224a lumen of dual lumen catheter 224's exit port 126. Contacting and attached to composition delivery container distal end 229, and in fluid connection with the interior of composition delivery container 227 is composition delivery catheter 224a, discussed below and shown in more detail in FIGS. 3A and 3B.

At catheter chamber 230, composition delivery catheter 224a and distension catheter 228 are brought adjacently together to form dual lumen composition delivery catheter 224. A proximal portion of dual lumen composition delivery catheter 224 is shown exiting catheter chamber 230 and entering proximal end 205a of the interior of insertion tube 205 (or into a catheter sleeve positioned in the interior of insertion tube 205, not shown).

Again referring to FIGS. 1 and 2, movement of dual lumen composition delivery catheter 224, so that exit port 126 moves away from or, or toward, catheter exit port 123, is effectuated by slidably moving slider 116a along slot 117a, which is positioned along the central axis of each of first side and second side of device 200 (not shown), in a proximal or distal direction. Referring to the first side only, though also found on the second side, finger slide 116a comprises an exterior side and an interior side, wherein the interior side is adjacent to slot 117a. The interior side of slider 116a is attached to slider prong 281a, which extends generally perpendicularly upward from catheter slide 243. Not shown, but present is the replicate slider prong 281b which is attached to slider 116b located on the exterior of casing side 201b (not shown), and is moveable in slot 117b, which is an opening defined by casing side 201b. Slider prong 281b extends generally perpendicularly downward from the side of catheter slide 243 opposite the side shown in FIG. 2. Catheter slide 243 has a slider prong 281a attached and extending upward perpendicularly from the first side of catheter slide 243, shown in FIG. 2, and catheter slide 243 also has a second slider prong 281b attached and extending downwardly (in relation to the position of FIG. 2) perpendicularly from the second side of catheter slide 243, not shown in FIG. 2. Moving either slider 116a or 116b from a proximal to a distal position, along the central axis, moves catheter slide 243 from a proximal to a distal position within the interior of handle 201, along the central axis. Moving catheter slide 243, in a proximal or distal direction, moves catheter chamber 203, which also moves both composition delivery catheter 224a, distension catheter 228, and dual lumen composition delivery catheter 224. Moving catheter chamber 230 in a distal direction, by moving slider 116a or 116b in a distal direction, causes dual lumen catheter 224 exit port 126 to move outwardly in a tangential direction away from catheter exit port 123 and away from insertion tube 205. Moving catheter chamber 230 in a proximal direction, by moving slider 116a or 116b in a proximal direction, causes dual lumen composition delivery catheter 224 exit port 126 to move inwardly in a tangential direction toward catheter exit port 123, and towards insertion tube 205.

Structures shown in and formed from the interior of casing 201b may provide stability and support for the components discussed herein. Rachet and pawl component 273 comprises one or more moveable pawls that interact with teeth defined on composition delivery container plunger stem 204 so that when composition delivery container plunger stem 204 is moved proximally or distally in a measured manner the movement can be heard and/or felt by an operator.

Figures 3A, 3B:
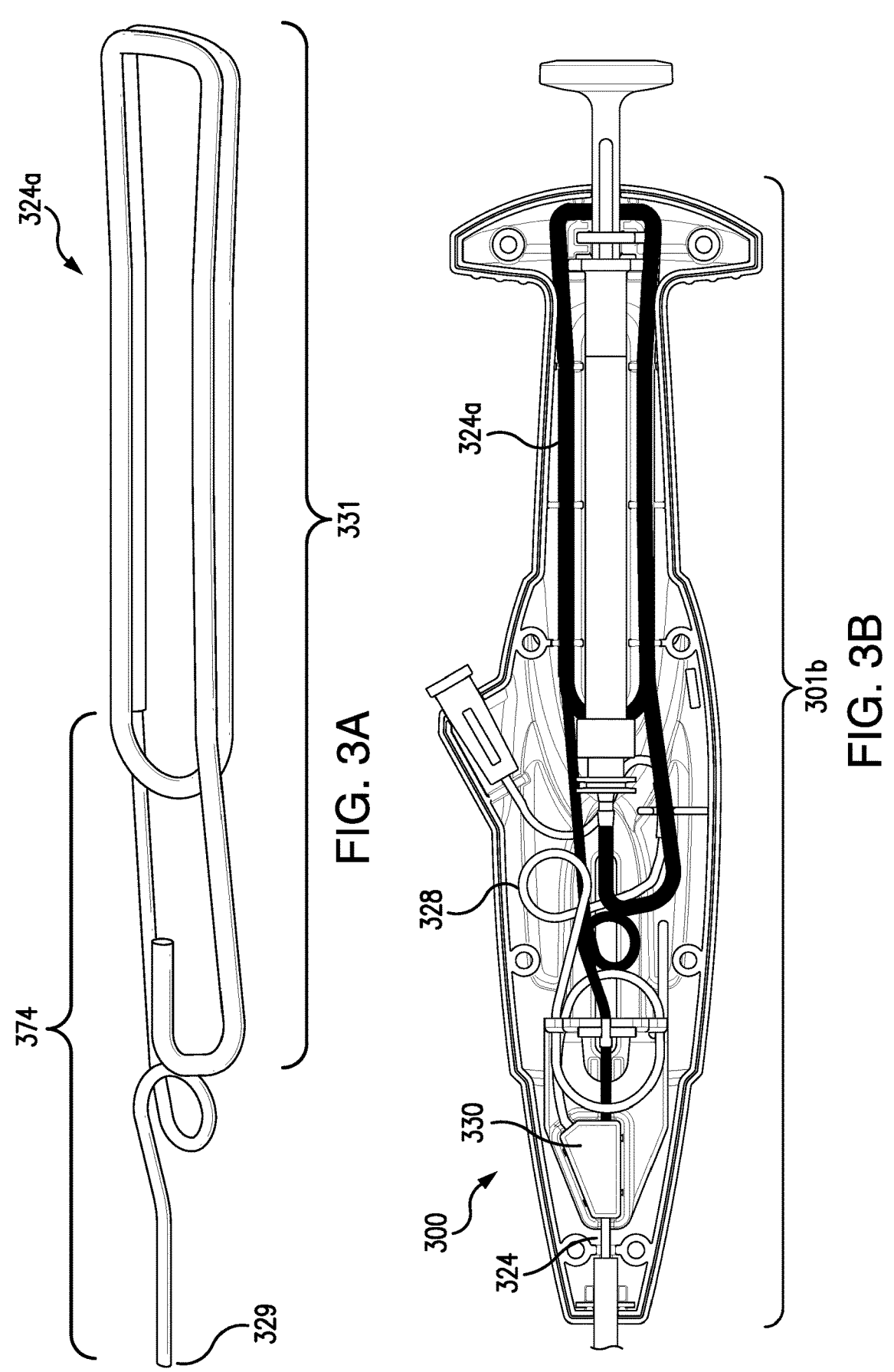
FIG. 3A shows a portion of a composition delivery catheter useful in an exemplary device of the present disclosure.
FIG. 3B shows the placement of this portion of a composition delivery catheter within the interior of a casing of an exemplary delivery device of the present disclosure.

FIG. 3A shows an isolated view of a portion of composition delivery catheter 324a, and FIG. 3B shows the placement of the portion of composition delivery catheter 324a within the interior of handle 301 of device 300. Shown in FIG. 3A, starting from distal end 329 of the portion of composition catheter 324a (which is in fluid connection with exit port 126 in FIG. 1) and proceeding proximally about one quarter to one third of the entire length of composition catheter 324a, composition catheter 324a has a smaller diameter region 374, which is followed proximally by a larger diameter region 331. In an aspect, composition delivery catheter 324a is a multi-diameter lumen catheter, in a distal to proximal direction, from a small diameter lumen to a larger diameter lumen. Composition delivery catheter 324a can contain the composition to be delivered. Because the amount of composition to be delivered is generally a small amount, which can be in a range from about 0.33 mL to about 1.5 mL, or from about 0.33 mL to about 1 mL, or from about 0.5 mL to about 1 mL, or from about 0.5 mL to about 1.5 mL, and/or all ranges thereinbetween, and can be valuable or unique, it is desired that the entire composition does not enter composition delivery container 227 (see FIG. 2), and optimally, little to none of the composition enters composition delivery container 227. Smaller diameter region 374 may have an interior diameter of from about 0.025 inches to about less than 0.060 inches; or from about 0.030 inches to about less than 0.060 inches; or from about 0.035 inches to about less than 0.060 inches; or from about 0.040 to about 0.050 inches; or from about 0.030 inches to about less than 0.060 inches; or from about 0.040 to about 0.060 inches, and/or all ranges thereinbetween. Larger diameter region 331 may have an interior diameter of from about greater than 0.060 inches to about 0.080 inches; or from about 0.062 inches to about 0.080 inches, or from about 0.064 inches to about 0.075 inches; or from about 0.066 inches to about 0.080 inches, or from about 0.068 inches to about 0.080 inches, or from about 0.070 inches to about 0.080 inches, or from about 0.060 inches to about 0.070 inches, and/or all ranges thereinbetween. FIG. 3A is an exemplary drawing of the folding of composition catheter 324*a* and is not intended to be limiting as to the length, folding or curvatures of a composition delivery catheter of the present disclosure. FIG. 3B shows placement of composition catheter 324*a* within the interior of a casing side, shown as 301*b* of exemplary delivery device 300. Also shown is catheter chamber 330 in which composition delivery catheter 324*a* (colored black) and distension catheter 328 meet to form dual lumen composition delivery catheter 324, of which one lumen is composition delivery catheter 324*a* to form exit port 126, and the lumen of distension catheter 328 for inflation of end structure 125. See also FIG. 5.

Figures 4A, 4B:
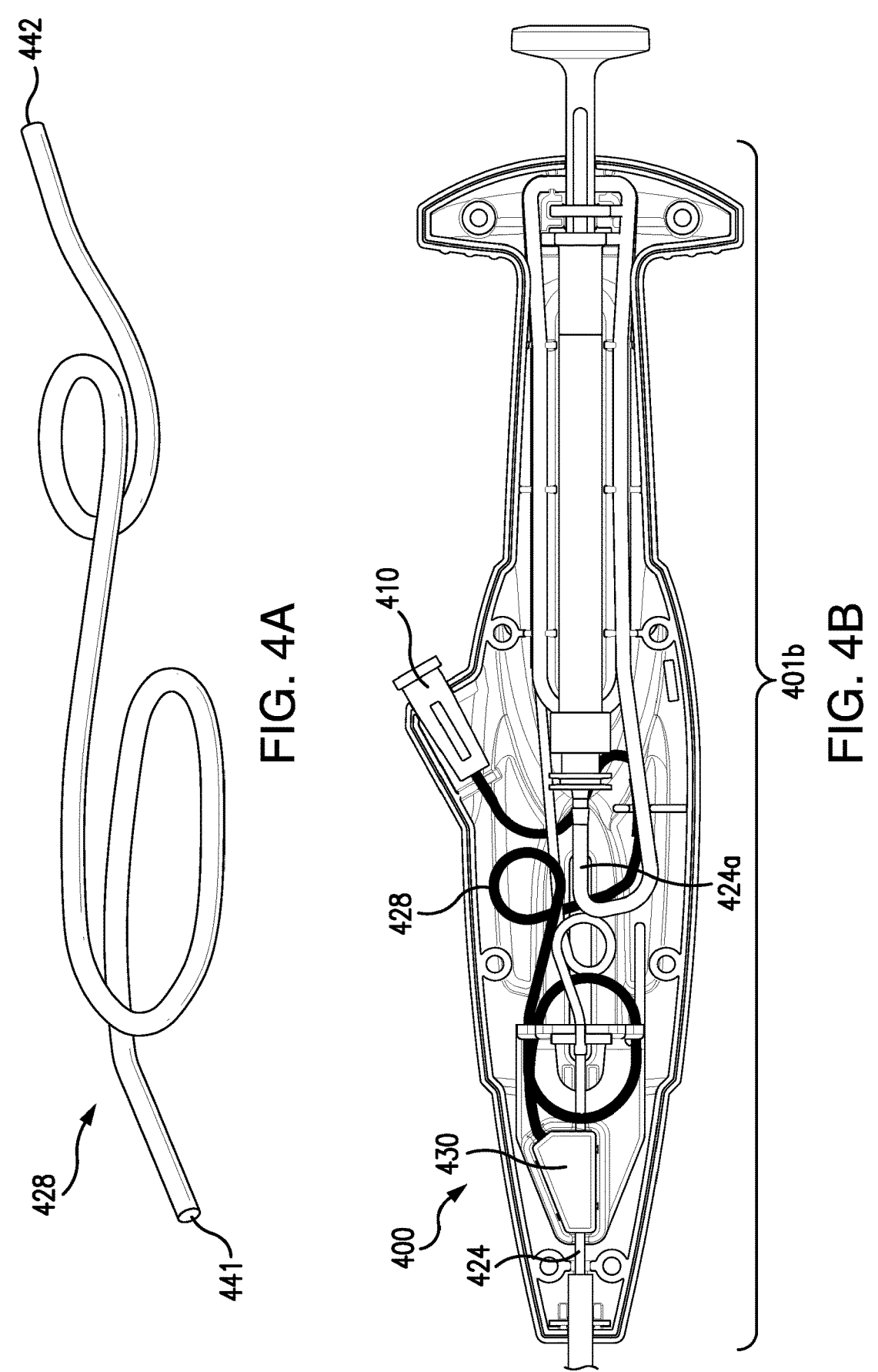
FIG. 4A shows a portion of a distension catheter useful in an exemplary device of the present disclosure.
FIG. 4B shows the placement of this portion of the distension catheter within the interior of a casing of an exemplary delivery device of the present disclosure.

FIG. 4A shows an isolated view of a portion of distension catheter 428 from proximal end 442 to location 441 which is where catheter 428 enters catheter chamber 430 (see 4B), and FIG. 4B shows the placement of this portion of distension catheter 428 within the interior of handle casing 401*b* of device 400. Distension catheter 428 is a continuous catheter tube in fluid connection with end structure 125, as a part of dual lumen catheter 424, through catheter chamber 430, and including area 441 of distension catheter 428 and continuing to 442 and in fluid connection with syringe connection 410 and distension syringe body. Proximal end 442 is in fluid connection with syringe attachment 410, so that when distension syringe 106 (shown in FIG. 1) is attached to the proximal side of syringe attachment 410, air or liquid can be moved into and out of distension catheter 428. For example, see FIG. 1, when end structure 125 is a balloon, air, gas or liquid contained within distension syringe body 108 is moved from distension syringe body 108 by distension plunger 107 into distension catheter 428 and then into end structure 125. By reversing the movement of distension plunger 107 (moving distension plunger 107 in a proximal direction), air, gas or fluid can be withdrawn from end structure 125 through distension catheter 428 which results in the collapse or shrinkage of end structure 125 (e.g., a balloon). FIG. 4A is an exemplary drawing of the folding of a portion of distension catheter 428 and is not intended to be limiting as to the length, folding or curvatures of a distension catheter of the present disclosure. FIG. 4B shows placement of distension catheter 428 within the interior of a handle casing side, shown as 401*b*. Also shown is catheter chamber 430 at which composition delivery catheter 424*a* and distension catheter 428 (shown in black), meet, adjacently, i.e., exterior side-to-exterior side, to form dual lumen composition delivery catheter 424.

Figure 5:
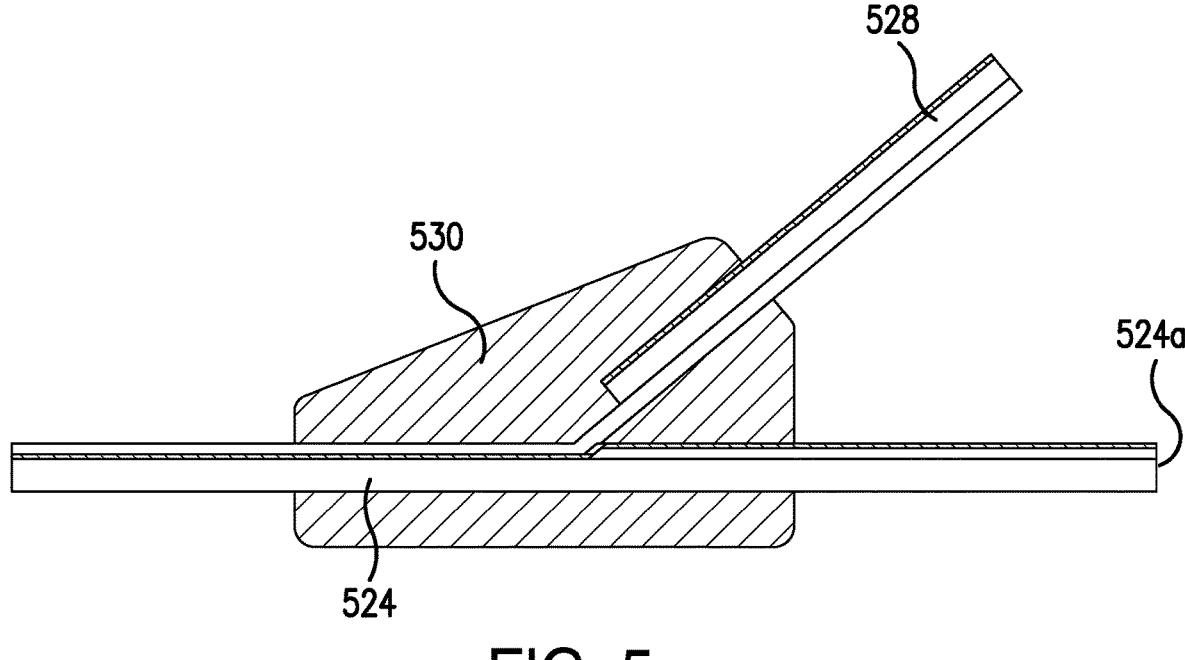
FIG. 5 shows a drawing of catheter chamber in which is shown the adjacent joining of a distension catheter with a composition delivery catheter to form the dual lumen delivery catheter.

FIG. 5 shows the interior of catheter chamber 530, and delivery catheter 524*a* and distension catheter 528. Dual lumen delivery catheter 524 comprises the lumens of composition delivery catheter 524*a* and distension catheter 528. Distension media, e.g., air, gas or saline, can be provided from distension syringe 106, through distension catheter 528, and into end structure 125 (shown in FIG. 1). As shown in FIG. 5, dual lumen composition delivery catheter 524 comprises one lumen which is composition delivery catheter 524*a* and a second lumen, which is distension catheter 528.

A delivery device of the present invention may comprise control components to aid in optimal results from use of a delivery device. In an aspect, a delivery device disclosed herein comprises one or more safety components, which may aid in the dual lumen catheter advancing from the catheter exit port of the insertion tube prior to the end structure, such as a balloon, is inflated. An exemplary safety component is shown in FIGS. 6A-6D. In 6A, a portion of alternative distension catheter 628 is shown, with an enlarged section 660, proximal end 642 and distal location 641. Enlarged section 660 is distal to and removed from proximal end 642. FIG. 6B shows the interior of a casing side, shown as 601*b* of exemplary delivery device 600, with finger slide 616 in place (and the top casing not present), and having finger slide 616*a* in its distal most position. Attached to catheter slide 643 is safety lock 661, which is a rod-like extension from catheter slide 643. Also shown is rib 662, on which enlarged section 660 of distension catheter 628 is positioned. Also shown, for reference, are catheter chamber 630, distension syringe 606, and composition delivery container 627.

FIG. 6C shows a perspective view of the interior of device 600 with components shown within one casing 601*b*, with finger slide 616*a* in place (and the top casing not present), and having finger slide 616*a* in its distal most position. Attached to catheter slide 643 is safety lock 661, which is a rod-like extension from catheter slide 643. Also shown is rib 662, on which enlarged section 660 of distension catheter 628 is positioned. Also shown, for reference, are catheter chamber 630, distension syringe 606, and composition delivery container 627.

FIG. 6D shows an enlarged view of a portion of the interior of delivery device 600 with components shown within one casing 601*b*, with finger slide 616*a* in place (and the top casing not present), and having finger slide 616 in its proximal most position. Attached to catheter slide 643 is safety lock 661, which is a rod-like extension from catheter slide 643, which by the movement of finger slide 161 to its most proximal position has moved safety lock 661 so that it contacts enlarged section 660 of distension catheter 628. Enlarged section 660 of distension catheter 628 is positioned on rib 662. In contacting enlarged section 660, safety lock 661 compresses the lumen of catheter 628 by forcing enlarged section 660 against rib 662 so that little to no distension fluid, air, gas or liquid, can traverse the lumen. This safety component ensures that end structure 125 (FIG. 1) is inflated only when the dual lumen catheter is extended from the insertion tube, which is when finger slide 616*a* (or 616*b*, not shown) is in its most distal position, pushing catheter slide 643 to its more distal position, and dual lumen exit port 126 has moved away from the insertion tube. Also shown, for reference, are catheter chamber 630, distension syringe 606, and composition delivery container 627.

An alternative component for control of distension of end structure 125 is shown in FIGS. 7A and 7B. In FIG. 7A, a portion of alternative distension catheter 728 is shown. Alternative distension catheter 728 comprises enlarged section 760 that is located proximally to proximal end 742 of alternative distension catheter 728. Alternative distension catheter continues in a distal direction through area 741 and into catheter chamber 730 where it is adjacently adjoined with a composition delivery catheter to form dual lumen catheter 724. Looking at FIG. 7B, movement of distension medium from a distension syringe into distension catheter 728 is prevented by downward pressure from lever 771 which compresses distension catheter 728 and prevents movement of distension medium from a distension syringe through distension catheter 728. As shown in FIG. 7B, lever 771 is not moved and is not compressing distension catheter 728. Lever 771 comprises flexible distal end 771a that overlays enlarged portion 760 of distension catheter 728. Not shown is a finger slide 116a or 116b, which controls movement of catheter slide 730. In FIG. 7B, catheter slide 730 is shown in its distal most position and comprises lever control 770, which is an blade-shaped extension from the proximal end of catheter slide 730. In FIG. 7B, lever control 770 is not contacting lever 771. When catheter slide 730 is moved in a proximal direction, lever control 770 slides above and over distal end 771a of lever 771, causing distal end 771a to compress enlarged portion 760 of distension catheter 728 and thus prevent passage of distension media through distension catheter 728. When catheter slide 730 is moved to a distal position, exit port 126 moves tangentially away from insertion tube 105 (see FIG. 1). With the movement of catheter slide 730 to this distal position, lever control 770 moves distally away from lever 771 and no longer contacts distal end 771a of lever 771, and distension catheter 728 is not compressed. Distension medium can then be provided to end structure 125.

A device disclosed herein functions so that substantially all of the composition to be delivered is delivered from the device to the intended target site, and there is minimal to no loss of the composition due to noticeable amount of composition remaining in the device itself. In an aspect, up to 100% of a composition is delivered by a disclosed device and/or method. In an aspect, about 99% of a composition is delivered by a disclosed device and/or method. In an aspect, about 98% of a composition is delivered by a disclosed device and/or method. In an aspect, about 97% of a composition is delivered by a disclosed device and/or method. In an aspect, about 96% of a composition is delivered by a disclosed device and/or method. In an aspect, about 95% of a composition is delivered by a disclosed device and/or method. In an aspect, about 94% of a composition is delivered by a disclosed device and/or method. In an aspect, about 93% of a composition is delivered by a disclosed device and/or method. In an aspect, about 92% of a composition is delivered by a disclosed device and/or method. In an aspect, about 91% of a composition is delivered by a disclosed device and/or method. In an aspect, about 90% of a composition is delivered by a disclosed device and/or method. In an aspect, greater than 85% of a composition is delivered by a disclosed device and/or method. In an aspect, greater than 87% of a composition is delivered by a disclosed device and/or method. In an aspect, greater than 80% of a composition is delivered by a disclosed device and/or method. In an aspect, greater than 75% of a composition is delivered by a disclosed device and/or method.

In an aspect, a method of providing a composition to a target site comprises contacting the target site with a composition that is delivered to the target site by a delivery device disclosed herein. A method may comprise steps that occur prior to contacting the target site with a composition, such as contacting the composition with the exit port 126 of the dual lumen catheter 124 and moving the composition container syringe 102 in a proximal direction to draw at least a portion of the composition through exit port 125 and into the composition delivery catheter 224a lumen of dual lumen catheter 124.

In an aspect, a method disclosed herein comprises contacting the dual lumen catheter 124 exit port 126 of delivery device disclosed herein with a composition to be delivered. The dual lumen catheter 124 exit port 126 is the distal end of composition delivery catheter 224a, and the other lumen of dual lumen catheter 124 is only in fluid connection with end structure 125, and not exit port 126. Thus, contacting the dual lumen composition delivery catheter exit port with a composition and moving the composition delivery container plunger 102 in a proximal direction causes the desired amount of the composition to be drawn into the lumen of the dual lumen catheter 124 that is composition delivery catheter 224a, for example, a catheter disclosed herein comprising a smaller diameter in a distal portion and a larger diameter in a proximal portion. By filling the delivery device (bringing the composition into the delivery device) by the dual lumen catheter 124 via exit port 126, and not allowing the composition to reside in the composition delivery container 127, a disclosed delivery device can provide substantially all of the desired amount of the composition to the target site. For example, the composition comprises sperm. The dual lumen catheter 124 exit port 126 contacts the sperm composition, and the entire composition is then drawn into the composition delivery catheter 224a lumen of the dual lumen catheter 124 by the proximal movement of the composition delivery container plunger 102, which creates a suction force throughout the lumen of the composition delivery catheter to dual catheter 124 exit port 126. When the composition delivery container plunger 102 is later moved in a distal direction, substantially all of the sperm in the sperm composition are delivered out the dual lumen catheter 124 exit port 126.

Disclosed herein is a method of delivering a composition to a target site comprising, providing a composition delivery device comprising a handle a composition delivery container and its plunger, an insertion tube, a dual lumen catheter comprising an end structure, components for moving the dual lumen catheter outwardly from and inwardly toward the insertion tube, optionally, components for distending the end structure, and fluid connections therefor.

A method for delivering a composition to a target site comprises the following steps:

Contacting a target site with a composition delivered from a delivery device comprising a handle a composition delivery container and its plunger, an insertion tube, a dual lumen catheter comprising an end structure, components for moving the dual lumen catheter outwardly from and inwardly toward the insertion tube, optionally, components for distending the end structure, and fluid connections therefor. The method further comprises a composition comprising a pharmaceutical composition comprising one or more of a gamete, sperm, ova, embryo, zygote, treatment agent, biological agent, radiographical agent, sonographical agent, active agent, and/or combinations thereof. The method further comprising wherein the target site is a cornua of a mammalian uterus, and the proximal ostium of a fallopian tube. After the delivery device is in place in the mammalian subject for a determined time period, the delivery device may be removed from the subject. Alternatively, prior to removal from the subject, the delivery device may be moved so that the exit port of the dual lumen catheter is in place at a second target site. For example, a second target site may be the other uterine cornua or fallopian tube proximal ostium. The second target site is contacted by at least a portion of the composition remaining in the delivery device. A further step may comprise removing the delivery device from the mammalian subject.

Steps prior to the contacting step may comprise: 1) a step of loading or filling the delivery device with the composition comprising a) inserting the exit port of the dual lumen catheter into a composition, such as a liquid composition in a container; b) moving composition delivery container plunger in a proximal direction, which creates a suction force to pull the composition into and through the exit port and into the composition catheter lumen of the dual lumen catheter, c) optionally before a) the exit port may be moved outwardly from the insertion tube by movement of a finger slide in a distal direction (which moves the catheter carrier in a distal direction, which moves dual lumen catheter in a distal direction, and moves the exit port of the dual lumen catheter away from catheter exit port of the insertion tube, and if this step of moving the dual lumen catheter exit port for ease of intaking the composition, a complementary step of returning the exit port to a location nearer the insertion may be accomplished by moving a finger slide in a proximal direction which then moves the catheter slide in a proximal direction which moves the dual lumen catheter in a proximal direction which moves the exit port of the dual lumen catheter closer to the insertion tube. 2) A step of insertion of the delivery device into a mammalian subject comprising wherein the insertion tube of a delivery device is accomplished by a) inserting through the cervix of a mammalian subject the insertion tube of a delivery device herein until the tip of the insertion tube contacts the fundus of the subject's uterus. Once the tip of the insertion tube is in place at the fundus of the uterus, the distal end of the dual lumen catheter, which comprises an exit port and an end structure can be extended. 3) A step of extending the exit port of the dual lumen catheter from the insertion tube so that the exit port and the end structure of the dual lumen catheter are at the target site comprising, a) moving a finger slide in a distal direction so that the catheter carrier is moved in a distal direction which moves the dual lumen catheter in a distal direction causing the distal end of the dual lumen catheter, comprising the exit port and an end structure to move away from the insertion tube in a tangential direction and toward and into the target site. 4) A step of expanding or inflating the end structure present on the dual lumen catheter comprises moving distension syringe plunger in a distal direction to push distension medium from the distension syringe body, wherein the distension syringe body was prefilled with distension medium. A preceding step may comprise attaching a distension syringe comprising distension medium and a distension syringe plunger to the distension inlet port of the handle of a delivery disclosed herein so that the attachment components, for example male/female luer lock, mate and form a fluid connection between the distension syringe body comprising distension medium and the distension catheter of the delivery device. A step of filling the distension syringe may precede the attachment of the distension syringe to the device, which comprises placing the distal end of the distension syringe within a distension composition, and start moving the distension syringe plunger in a proximal direction to draw distension medium into the syringe body. Components for attachment of a syringe to a catheter are known to those of skill in the art, and such known attachment components are contemplated by the present invention and can replace the exemplified luer lock attachment components. Once the distension syringe plunger has moved to its most distal position, a syringe lock may be engaged to stably maintain the distension plunger head in its distal position. A distension syringe disclosed herein may comprise a syringe lock for stably maintaining the distension plunger head in a distal position.

A delivery device disclosed herein may comprise control components that prevent distension medium from filling/ inflating the end structure of the dual lumen catheter, and methods for controlling inflation of the end structure of the dual lumen catheter. A control component comprises a distension catheter comprising an enlarged section. The distension catheter may comprise an enlarged section, which may comprise a thickened wall of the catheter in a limited size section or may comprise a sleeve on the outer surface of the catheter forming a limited size enlarged section on the catheter. One enlarged section may be located at distally removed site from the proximal end of the distension catheter so that when the distension catheter is positioned in a delivery device, the enlarged section overlies a rib formed in the interior of one side casing of the handle of the delivery device. The rib is removed in a proximal direction from a safety lock, which is a rod extending from the catheter carrier. When the catheter carrier is in its proximal most location, the safety lock overrides and compresses the enlarged section of the distension catheter between the safety lock and the rib. In a compressed state, the enlarged section prevents distension medium from reaching the end structure of the dual lumen catheter, and thus, no inflation of the end structure occurs.

A method of control of inflation of the dual lumen catheter end structure may comprise a) moving or positioning the catheter slide comprising a safety lock, to its proximal most location wherein the safety lock compresses an enlarged section of the distension catheter. Moving the catheter slide, by moving a finger slide attached via a prong to the catheter slide, in a distal direction removes the safety lock from contact with the enlarged section, which allows distal movement of the distension syringe plunger to push distension medium into and through the distension catheter so that the dual lumen catheter end structure is inflated.

Alternatively, control components may comprise a lever and a distension catheter having an enlarged section that is in a more proximal location than that of the enlarged section above. The enlarged section may comprise a thickened wall of the catheter in a limited size section or may comprise a sleeve on the outer surface of the catheter forming a limited size enlarged section on the catheter. The lever is attached in the interior of the delivery device handle adjacent to the proximal end of the distension catheter distal to the catheter attachment components. The enlarged section is positioned so that it lies under the flexible end of the lever and may be positioned between the end of the lever (on the upward side of the catheter) and a rib (on the underside of the catheter) formed in the interior of one side casing of the handle of the delivery device. The catheter slide comprises a blade-shaped protrusion positioned so that when the catheter slide is in its proximal most position, the blade-shaped protrusion overrides the flexible lever end, moving the lever end in a downward direction so that it compresses this enlarged section of the distension catheter. A method of control of inflation of the dual lumen catheter end structure may comprise a) moving or positioning the catheter slide comprising a blade-shaped protrusion, to its proximal most location wherein the a blade-shaped protrusion overrides and moves a lever end in a downward direction so that the lever end compresses the enlarged section of the distension catheter. Moving the catheter slide, by moving a finger slide attached via a prong to the catheter slide, in a distal direction removes the blade-shaped protrusion from contact with the lever end, which allows the lever end to return to a position where it does not contact the enlarged section of the distension catheter, which allows distal movement of the distension syringe plunger to push distension medium into and through the distension catheter so that the dual lumen catheter end structure is inflated.

A method for delivering a composition to a target site comprises the following steps:

1) Providing a composition delivery device comprising a handle and an insertion tube having a catheter exit port proximal to the closed tip of the insertion tube, a composition delivery container and its plunger, a dual lumen catheter comprising as one of its two lumens the composition delivery catheter and comprising as its second lumen, the lumen of the distension catheter; and fluid connections therefor; wherein the handle comprises a. a composition delivery container, contained within the handle, in fluid connection with the composition delivery catheter, and having a composition delivery plunger slidably disposed therein the composition delivery container; and the insertion tube enclosing the dual lumen composition delivery catheter disposed within the insertion tube and the insertion tube comprising a catheter exit port;

b. a pair of finger slides, each slidably disposed in a slot formed through each side of a casing forming the handle, wherein the interior surface of each finger slide is attached via a prong to a catheter slide residing inside the handle;

c. a distension inlet port, in fluid connection with a distension catheter, wherein the distension catheter is in fluid connection with the end device of the dual lumen catheter;

2) Moving the exit port of the dual lumen catheter outwardly from the interior of the insertion tube through or away from the catheter exit port of the insertion tube by moving a finger slide in a distal direction which moves the catheter slide in a distal direction so that the dual lumen catheter moves and the exit port of the dual lumen catheter moves outwardly and away from the catheter exit port of the insertion tube;

3) contacting the exit port of the dual lumen catheter with a disclosed composition and moving the composition delivery plunger in a proximal direction to draw at least a portion of the composition into the lumen of the composition delivery catheter;

4) moving the exit port of the dual lumen catheter inwardly to the catheter exit port of the insertion tube by moving a finger slide in a proximal direction which moves the catheter slide in a proximal direction so that the dual lumen catheter moves so that the exit port of the dual lumen catheter moves inwardly and toward the catheter exit port;

5) inserting the insertion tube into a uterus of a mammalian female so that the tip of the insertion tube, which may be an atraumatic tip, is at the fundus of the uterus and extending the exit port of the dual lumen composition delivery catheter as in step 2 so that the end structure of the dual lumen catheter is positioned at the target site, for example, at a cornua of the uterus, near or adjacent to the proximal ostium of the fallopian tube;

6) before or after the above steps, attaching a distension syringe, comprising a syringe body and a syringe plunger slidably disposed therein and comprising distension medium, and optionally comprising a syringe lock, to the distension inlet port of the handle so that the distension syringe body in in fluid connection through the distension catheter to the dual lumen catheter end structure; and moving the distension syringe plunger in a distal direction to move distension medium (air, gas or liquid) from the distension syringe body into and through the distension catheter so that the end structure is inflated and contains air, gas or fluid; optionally, engaging the distension syringe plunger with the syringe lock so as to stabilize and prevent movement of the distension syringe plunger;

7) moving the composition delivery container plunger in a distal direction so that the composition is moved through composition delivery catheter and out the exit port of the dual lumen catheter and is delivered to the target site; optionally engaging a rachet and pawl mechanism of the plunger, so that the plunger movement is heard and/or felt by the device operator;

8) optionally, maintaining the end structure of the dual lumen catheter in its position for a predetermined time to allow the composition to remain at the target site;

9) disengaging the syringe lock and moving the distension syringe plunger in a proximal direction to deflate the end structure of the dual lumen catheter;

10) retracting the exit port of the dual lumen catheter to its position in or adjacent to the catheter exit port of the insertion tube by moving the finger slide in a proximal direction which causes the catheter slide to move in a proximal direction;

11) withdrawing the insertion tube from the mammalian female.

Before step 11, delivery of a portion of the composition may be provided to a second fallopian tube by rotating the device 180 degrees and extending the dual lumen composition delivery catheter so that the exit port of the dual lumen composition delivery catheter is positioned at a second target site, expanding the end structure, if needed, and delivering at least a portion of the composition to a second fallopian tube. The applicable above method steps for extending the dual lumen composition delivery catheter, inflating the end structure, delivering the composition, deflating the end structure, withdrawing the dual lumen composition delivery catheter, are repeated for the second fallopian tube prior to and then withdrawing the insertion tube from the female. A predetermined time for holding the delivered composition at the target site may be 0 to 5 minutes, for example, 0, 1, 2, 3, 4, or 5 minutes, or any times thereinbetween.

Compositions that comprise an effective amount of an active agent useful in treating pathologies or diseases of the fallopian tube can be used with the disclosed devices and methods. Compositions that comprise an effective amount of an active agent useful in treating or alleviating infertility can be used with the disclosed devices and methods. Compositions comprising an effective amount of sperm can be used with the disclosed devices and methods. Compositions known to be used for intrauterine insemination (IUI) can be used with the disclosed devices and methods. Compositions may comprise cells, sperm, ova, zygotes, embryos or combinations thereof and/or with other compounds, molecules or tissues. Compositions disclosed herein may comprise pharmaceutical compositions.

Methods for therapeutic or diagnostic treatments may be provided to humans or animals by delivering therapeutic compositions comprising an effective amount of therapeutic agents or diagnostic compositions, such as contrast media compositions, to a subject's bodily structure by using the delivery device as described herein. For example, diagnostic compositions may be provided to a fallopian tube or both fallopian tubes to evaluate the condition of the tube, such as tubal occlusion, tubal patency, hydrosalpinx, or pyosalpinx. Diagnostic compositions comprising an effective amount of compounds or molecules, such as radiographic materials, radiopaque dye, saline and air contrast, saline, or combinations thereof, can be used in methods to evaluate a subject's bodily structures by imaging, such as, radiographically, fluoroscopically or sonographically.

For example, therapeutic compositions, comprising an effective amount of a therapeutic active agent, cells, compounds or molecules, or combinations thereof, may be provided to a fallopian tube or both fallopian tubes to enhance fertility. Therapeutic compositions may comprise sperm, which can be processed or washed in known methods and/or compositions, hormones for fertility, fertility enhancing compounds, gametes, ova, combinations of sperm and ova, one or more zygotes, or one or more embryos, gamete and embryo deposition, ovarian stimulating compounds or gonadotropins (i.e., Follistim, Gonal-F, Repronex, Menopur, Bravelle, letrozole), ovulation induction compounds (i.e., Clomiphene citrate, such as Clomid or Serophene), oviductal glycoproteins, compounds to reduce the likelihood of implantation failure (fertilized egg) or miscarriage (i.e., granulocyte colony stimulating factor, additives from the group consisting of cytokines that suppress TH1 immune response, enhance TH2 immune response, anti-inflammatory agents, inhibitors of pro-inflammatory cytokines), hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds or combinations thereof.

For example, therapeutic compositions comprising an effective amount of a therapeutic active agent, cells, compounds or molecules, or combinations thereof, may be provided to a fallopian tube or both fallopian tubes to treat disorders, infections or cancer near, in, around, at the cornua, proximal ostium, or fimbriae exit of the fallopian tube, such as for treating ectopic pregnancy, salpingitis (i.e., pelvic inflammatory disease), tubal spasm, tubal occlusion (i.e., providing shockwaves, chemical means including solvents, biological means including enzymes, or mechanical means including stiff or cutting catheter ends), tubal obstruction, tubal obliteration (i.e., silver nitrate), tubal disease, manage tubal condition pre, during or post treatment, tubo-ovarian abscess, paratubal cysts, ovarian cysts, benign tubal tumors, benign ovarian tumors, tubal cancer, ovarian cancer, prophylactic treatment of tube or ovaries. Therapeutic compositions comprise compounds to treat ectopic pregnancies (i.e., methotrexate, PGF2a, or hypertonic glucose solution), compounds to treat fallopian tube occlusions (i.e., Ringer's lactate solution, Solu-Cortef, heparin to cleanse and maintain fallopian tube patency), compounds for pain management (i.e., lidocaine, lignocaine, bupivacaine, mepivacaine), antibiotics (i.e., doxycycline), narcotics, medications, hydrocortisone, anti-inflammatory, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, compounds for cancer or anti-cancer drugs (i.e., radioactive compounds, paclitaxel, cisplatin, platinum-taxane, carboplatin, cyclophosphamide, docetaxel), other compounds that may treat or prevent conditions related to the fallopian tube, uterus, ovaries, peritoneum, or other organs or coverings reached by a composition flowing from the cornua or ostia of a fallopian tube or combinations thereof.

Compositions used as described herein with devices of the present invention can be incorporated in a carrier, depot, injectable, capsule, particles, vessel, gels, fibers, or equivalent means for immediate, controlled, extended or sustained release of one or more compositions. Compositions may display a narrower therapeutic range, where controlling the release of the compound is necessary to effectively treat. For example, extending the release of a compound may be achieved through the manipulation of physiochemical properties, the use of formulation technologies such as microspheres and nanospheres, and balancing the in vivo properties of the compound (such as half-life). Compositions disclosed herein may comprise a pharmaceutically acceptable composition comprising pharmaceutical formulation agents, compounds or molecules. A pharmaceutically acceptable composition may comprise compounds or molecules such as diluents, excipients, solution- or diffusion-enhancing compositions, surfactants, buffers, porogens, pH modulators, antioxidants, lipids, salts, vitamins, energy molecules (e.g., ATP, glucose) or other known formulation compounds or molecules for treatments or diagnoses of subjects.

Post-procedure methods and compositions may further comprise the use of hormonal agents compositions in methods to prohibit menstrual shedding of the endometrium are also contemplated to minimize the risk of expulsion for a period of time, for example to allow for a continued period of time for resorption of the composition. For example, a method comprising administration of a composition comprising an effective amount of a long-acting hormonal medication such as an injectable medroxyprogesterone acetate depot may serve the function of both the pre- and post-operative hormonal therapy without the need for reliance on patient compliance. Post-operative methods and compositions may further comprise methods providing an effective amount of antibiotic or steroidal compositions.

In methods where delivery of such therapeutic or diagnostic compositions are provided by directly providing such compositions to a target site or sites, such as use of a delivery device disclosed herein, the compositions may further comprise multiple steps of delivery comprising delivery of a diagnostic compound initially, followed by a therapeutic composition, and the delivery of the diagnostic or therapeutic compositions may be monitored, viewed or assisted by techniques such as ultrasound. A composition comprising therapeutic agents or diagnostic compounds may be provided as one composition or may be sequentially provided in separate compositions using a delivery device of the present invention and may provide both treatment and diagnosis of the condition of a structure in one step or multiple steps of delivering the one or more compositions. Alternatively, the therapeutic agent composition or a combined therapeutic/diagnostic agents composition may be delivered to limit or locate the medicament in the targeted structure with or without the support of imaging allowing for treatment to occur with or without diagnosis sequentially or simultaneously.

A system of the present disclosure comprises providing a device disclosed herein, or a device disclosed herein with a composition disclosed herein. A system disclosed herein comprises a device disclosed herein, a distension syringe, and optionally, a composition disclosed herein. A system disclosed herein comprises a device disclosed herein having a safety lock, a distension syringe, and optionally, a composition disclosed herein. A system disclosed herein comprises a device disclosed herein comprising a safety lock, a distension syringe comprising a syringe lock, and optionally, a composition disclosed herein. A system and/or a device disclosed herein may be packaged in a sterile container.

A kit of the present invention comprises a device disclosed herein which is contained in a kit container, and optionally with directions for use of the device. A kit of the present disclosure comprises a container containing a device disclosed herein, with a composition disclosed herein, and optionally directions for delivering the composition with the device. A kit disclosed herein comprises a container comprising a device disclosed herein, a distension syringe, and optionally, a composition disclosed herein, with directions for delivering the composition with the device. A kit disclosed herein comprises a container comprising a device disclosed herein having a safety lock, a distension syringe, and optionally, a composition disclosed herein with directions for delivering the composition with the device. A kit disclosed herein comprises a container comprising a device disclosed herein comprising a safety lock, a distension syringe comprising a syringe lock, and optionally, with directions for delivering the composition with the device. A kit and/or a device disclosed herein may be packaged in a sterile container. A kit disclosed above may further comprise a composition disclosed herein.

EXAMPLES

Example 1 Fluid Delivery Evaluation of a Method and Delivery Device

Using a calibrated pipettor, place distilled water (composition) into a container. Weigh a delivery device as disclosed herein and record the weight. Direct exit port of dual lumen composition delivery catheter into the composition in the container.

While keeping exit port of dual lumen composition delivery catheter submerged in the composition, draw fluid into the delivery device by pulling back on the plunger. Weigh the filled device and record the weight.

Place the exit port of dual lumen composition delivery catheter inside an empty pre-weighed vial to collect the dispensed fluid.

While supporting the delivery device with one hand, advance the composition container plunger with the other hand to dispense the fluid. Weigh the delivery device after dispensing and record the weight. Determine the percent fluid delivery using the following formula:

$$^*\text{Delivery percent} = \left[(B - C)/(B - A)\right] \times 100\%$$

a. A=Mass of device prior to filling (g) B=Mass of filled (aspirated) device (g) C=Mass of device after dispensing (g)

Results of Fluid Delivery Testing

| Report ID | # Devices Tested | Average % Delivered |
|---|---|---|
| 02061 | 29 | 99.5% |
| 02064 | 29 | 99.5% |

Example 2 Human Sperm Survival Assay (HSSA) Summary Testing

Description of Test:

Sperm was prepared and drawn into a delivery device disclosed herein and placed in a 32° C. incubator for 30 minutes. The medium was expelled from the delivery device after 30-minutes and incubated for 72-hours. The forward progressive motility was read and recorded at the beginning of the assay, at 24-hours, 48-hours, and 72-hours. Results:

| Sample ID | Sample Type | Initial Motility | Motility @24 hr* | Motility @48 hr | Motility @72 hr |
|---|---|---|---|---|---|
| 4658 | Control | 100% | 97% | 91% | 84% |
| | Test Article | 100% | 98% | 94% | 90% |
| 4666 | Control | 100% | 97% | 91% | 84% |
| | Test Article | 100% | 96% | 89% | 83% |
| 4668 | Control | 100% | 97% | 91% | 84% |
| | Test Article | 100% | 94% | 89% | 82% |

The data show that there was >80% motility at 24 hours after exposure in the lumen of the composition delivery catheter having a smaller lumen followed by a larger lumen. This is in contrast to the HSSA specification referenced in 510K submissions as recent as 2017, which showed equal to 70% motility at 24 hours Definitions As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, EIZ specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, when a compound is referred to as a monomer or a compound, it is understood that this is not interpreted as one molecule or one compound. For example, two monomers generally refers to two different monomers, and not two molecules.

As used herein, the terms "optional" or "optionally" means that the subsequently described event or circumstance can or cannot occur, and that the description includes instances where said event or circumstance occurs and instances where it does not.

As used herein, the terms "about," "approximate," and "at or about" mean that the amount or value in question can be the exact value designated or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In an aspect, a mammalian subject is a human. A patient refers to a subject afflicted with a disease or disorder or requiring contraception. The term "patient" includes human and veterinary subjects.

As used herein, the terms "administering" and "administration" refer to any method of providing a disclosed composition to a subject.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The transitional phrase "consisting of" excludes any element, step, or ingredient not specified in the claim, closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" limits the scope of a claim to the specified materials or steps and those that do not materially affect the basic and novel characteristic(s) of the claimed invention. A 'consisting essentially of' claim occupies a middle ground between closed claims that are written in a 'consisting of format and fully open claims that are drafted in a 'comprising' format. Optional additives as defined herein, at a level that is appropriate for such additives, and minor impurities are not excluded from a composition by the term "consisting essentially of".

When a composition, a process, a structure, or a portion of a composition, a process, or a structure, is described herein using an open-ended term such as "comprising," unless otherwise stated the description also includes an embodiment that "consists essentially of" or "consists of" the elements of the composition, the process, the structure, or the portion of the composition, the process, or the structure.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

The term "or", as used herein, is inclusive; that is, the phrase "A or B" means "A, B, or both A and B". More specifically, a condition "A or B" is satisfied by any one of the following: A is true (or present) and B is false (or not present); A is false (or not present) and B is true (or present); or both A and B are true (or present). Exclusive "or" is designated herein by terms such as "either A or B" and "one of A or B", for example.

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "effective amount" denotes the amount of a medicament or of a pharmaceutically active ingredient which causes a biological or medical response in a tissue, system, animal or human which is sought or desired, for example, by a researcher, physician or subject. In addition, the term "effective amount denotes an amount which, compared with a corresponding subject who has not taken this amount, has the following consequence: improved treatment, healing, prevent or elimination of a disease, condition, syndrome, disease state, complaint, disorder or prevention of side effects or also the reduction in the progress of a disease, complaint or disorder. The term "effective amount" also encompasses the amounts which are effective for increasing nor physiological function.

When materials, methods, or machinery are described herein with the term "known to those of skill in the art", "conventional" or a synonymous word or phrase, the term signifies that materials, methods, and machinery that are conventional at the time of filing the present application are encompassed by this description. Also encompassed are materials, methods, and machinery that are not presently conventional, but that will have become recognized in the art as suitable for a similar purpose.

Unless stated otherwise, all percentages, parts, ratios, and like amounts, are defined by weight.

All patents, patent applications and references included herein are specifically incorporated by reference in their entireties.

It should be understood, of course, that the foregoing relates only to embodiments of the present disclosure and that numerous modifications or alterations may be made therein without departing from the spirit and the scope of the disclosure as set forth in this disclosure.

The present disclosure is further illustrated by the examples contained herein, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present disclosure and/or the scope of the appended claims.

Although the exemplary embodiments of the present invention describe in detail methods, delivery systems, and compositions to diagnosis or treat the fallopian tubes of human, the present invention is not limited to these embodiments. There are numerous modifications or alterations that may suggest themselves to those skilled in the art for use of the methods, delivery systems, and compositions herein for the diagnosis or treatment of a variety of conduits in both human and non-human mammals.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

What is claimed is:

1. A device for providing a composition comprising gametes or embryos to a uterus of a subject, comprising, a handle; an insertion tube; a composition delivery container comprising a composition delivery container syringe and plunger, a composition delivery catheter having a proximal end and a distal end, wherein the proximal end of the composition delivery catheter is in fluid connection with the composition delivery container and the distal end of the composition delivery catheter is an exit port for entry and exit of the composition; wherein proximal movement of the composition delivery container plunger draws a composition into the exit port, and distal movement of the composition delivery container plunger expels the composition from the exit port; a distension syringe comprising a distension syringe body and a distension syringe plunger having a distension plunger head; a distension catheter, having a proximal end and a distal end, and comprising an enlarged section located proximally to the proximal end of the distension catheter, wherein the enlarged section is contactable by a lever so that downward pressure by the lever compresses the enlarged section and prevents passage of distension media through distension catheter, wherein the proximal end of the distension catheter is in fluid connection with the distension syringe comprising a distension syringe plunger, and the distal end of the distension catheter is in fluid connection with an end structure, wherein adjacently connecting the distension catheter and the composition delivery catheter forms a dual lumen catheter having the exit port and the end structure;, a catheter carrier for moving the dual lumen catheter outwardly from and inwardly toward the insertion tube.

2. The delivery device of claim 1, wherein the distension syringe comprises a syringe body and a syringe plunger comprising a plunger head, a syringe lock comprising an end piece attached to and encircling the exterior of the proximal end of the distension syringe body; two finger pinch clamps, each comprising a pincer, spaced 180 degrees apart on the exterior edge of the end piece, and movably affixed to the end piece, for stabilizing the distension syringe plunger by securing the plunger head within the two pincers of the finger pinch clamps.

3. A method for providing a composition comprising one or more of gametes or embryos to at least one site in a uterus in a subject comprising,
    a) loading the composition into the delivery device of claim 1 by i) inserting the exit port of the composition delivery catheter into the composition; ii) moving the composition delivery container plunger in a proximal direction, bringing the composition into and through the exit port and into the composition delivery catheter lumen;
    b) inserting the insertion tube of the delivery device into a mammalian subject through the cervix of the mammalian subject until the tip of the insertion tube contacts the fundus of the subject's uterus, and optionally moving a depth stop located on the insertion tube to mark the depth of insertion of the insertion tube;
    c) extending the dual lumen catheter's exit port and end structure from the insertion tube to the target site by moving the finger slide in a distal direction so that the catheter carrier is moved in a distal direction which moves the dual lumen catheter in a distal direction causing the distal end of the dual lumen catheter to move away from the insertion tube in a tangential direction and toward and into the target site;
    d) inflating the end structure of the dual lumen catheter comprising filing the distension syringe with a distension fluid and then moving the distension syringe plunger in a distal direction to push the distension medium from the distension syringe body into the end structure;
    e) moving the composition delivery container plunger in a distal direction to move at least a portion of the composition through the composition delivery catheter lumen and out the exit port and to the target site;
    f) maintaining the end structure and exit port at the target site for a predetermined time so as to contact the target site with the composition.

4. The method of claim 3, further comprising g, retracting the dual lumen catheter end structure and exit port toward the insertion tube.

5. The method of claim 4, further comprising h, rotating the delivery device 180 degrees and extending the dual lumen catheter end structure and exit port to a second target site, and delivering an amount of the composition.

6. The method of claim 5, further comprising i, maintaining the end structure and exit port at the target site for a predetermined time so as to contact the second target site with the composition.

7. The method of claim 6, further comprising j, removing the insertion tube from the subject.

8. The method of claim 3, wherein the target site is the uterine cornua of a fallopian tube.

9. The method of claims 5, wherein the target site is the uterine cornua of a fallopian tube.

10. The method of claim 3, wherein the composition comprises cells, sperm, ova, zygotes, embryos or combinations thereof, and optionally, comprising other compounds, molecules or tissues.

11. The method of claim 3, wherein the composition comprises an effective amount of a therapeutic active agent, cells, compounds or molecules, or combinations thereof, sperm, hormones for fertility, fertility enhancing compounds, gametes, ova, combinations of sperm and ova, one or more zygotes, or one or more embryos, gamete and embryo deposition, ovarian stimulating compounds or gonadotropins (i.e., Follistim, Gonal-F, Repronex, Menopur, Bravelle, letrozole), ovulation induction compounds (i.e., Clomiphene citrate, such as Clomid or Serophene), oviductal glycoproteins, compounds to reduce the likelihood of implantation failure (fertilized egg) or miscarriage (i.e., granulocyte colony stimulating factor, additives from the group consisting of cytokines that suppress THI immune response, enhance TH2 immune response, anti-inflammatory agents, inhibitors of pro-inflammatory cytokines), hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds or combinations thereof.

\* \* \* \* \*